United States Patent
Kilbacak et al.

(10) Patent No.: US 12,364,628 B2
(45) Date of Patent: Jul. 22, 2025

(54) ABSORBENT ARTICLES INCLUDING FRONT AND BACK WAIST PANELS WITH DIFFERENT STRETCH CHARACTERISTICS

(71) Applicant: The Procter & Gamble Company, Cincinnati, OH (US)

(72) Inventors: Sally Lin Kilbacak, Cincinnati, OH (US); Donald Carroll Roe, West Chester, OH (US); Jeromy Thomas Raycheck, Cincinnati, OH (US); Uwe Schneider, Cincinnati, OH (US); Michael Devin Long, Harrison Township, OH (US); Michael Brian Quade, Blue Ash, OH (US); Jason Edward Naylor, Loveland, OH (US); Jeffry Rosiak, Loveland, OH (US); Stephen Joseph Lange, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 735 days.

(21) Appl. No.: 17/242,376

(22) Filed: Apr. 28, 2021

(65) Prior Publication Data
US 2021/0346213 A1 Nov. 11, 2021

Related U.S. Application Data

(60) Provisional application No. 63/020,043, filed on May 5, 2020.

(51) Int. Cl.
*A61F 13/49* (2006.01)
*A61F 13/15* (2006.01)
*A61F 13/494* (2006.01)

(52) U.S. Cl.
CPC .. *A61F 13/49012* (2013.01); *A61F 13/15593* (2013.01); *A61F 13/49413* (2013.01);
(Continued)

(58) Field of Classification Search
None
See application file for complete search history.

(56) References Cited

U.S. PATENT DOCUMENTS 3,091,550 A 5/1963 Doying
3,113,225 A 12/1963 Claus
(Continued)

FOREIGN PATENT DOCUMENTS

CN 1144472 A 3/1997
CN 1224606 A 8/1999
(Continued)

OTHER PUBLICATIONS

All Office Actions; U.S. Appl. No. 18/493,083, filed Oct. 24, 2023.
(Continued)

*Primary Examiner* — Michele Kidwell
(74) *Attorney, Agent, or Firm* — Charles R. Matson

(57) ABSTRACT

Aspects of the present disclosure relate to absorbent articles with front and back waist panels having different stretch characteristics. A first waist panel may be connected with a chassis and positioned in a first waist region, and a second waist panel may be connected with the chassis and positioned in a second waist region. In some configurations, the first waist panel may comprise a first structural feature that is not included in the second waist panel or may comprise a first structural feature is different from a second structural feature included in the second waist panel. As such, the first structural feature provides different stretch characteristics between the first waist panel and the second waist panel.

11 Claims, 24 Drawing Sheets

(52) U.S. Cl.
CPC .............. *A61F 2013/15869* (2013.01); *A61F 2013/15878* (2013.01); *A61F 2013/1591* (2013.01); *A61F 2013/49098* (2013.01); *A61F 2013/4944* (2013.01)

(56) References Cited

U.S. PATENT DOCUMENTS

| | | |
|---|---|---|
| 3,562,041 A | 2/1971 | Robertson |
| 3,733,238 A | 5/1973 | Long |
| 3,848,594 A | 11/1974 | Buell |
| 3,881,488 A | 5/1975 | Delanty et al. |
| 4,116,892 A | 9/1978 | Schwarz |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit |
| 4,556,146 A | 12/1985 | Swanson et al. |
| 4,568,344 A | 2/1986 | Suzuki et al. |
| 4,589,876 A | 5/1986 | Van Tilburg |
| 4,610,678 A | 9/1986 | Weisman |
| 4,662,875 A | 5/1987 | Hirotsu |
| 4,673,402 A | 6/1987 | Weisman |
| 4,687,478 A | 8/1987 | Van Tillburg |
| 4,695,278 A | 9/1987 | Lawson |
| 4,704,115 A | 11/1987 | Buell |
| 4,795,454 A | 1/1989 | Dragoo |
| 4,795,510 A | 1/1989 | Wittrock et al. |
| 4,824,498 A | 4/1989 | Goodwin et al. |
| 4,834,735 A | 5/1989 | Alemany |
| 4,834,741 A | 5/1989 | Sabee |
| 4,846,815 A | 7/1989 | Scripps |
| 4,854,984 A | 8/1989 | Ball |
| 4,888,231 A | 12/1989 | Angstadt |
| 4,894,060 A | 1/1990 | Nestegard |
| 4,909,803 A | 3/1990 | Aziz |
| 3,860,003 B2 | 6/1990 | Buell |
| 4,940,464 A | 7/1990 | Van Gompel |
| 4,946,527 A | 8/1990 | Battrell |
| 4,950,264 A | 8/1990 | Osborn, III |
| 5,009,653 A | 4/1991 | Osborn, III |
| 5,026,364 A | 6/1991 | Robertson |
| 5,092,861 A | 3/1992 | Nomura |
| 5,110,403 A | 5/1992 | Ehlert |
| 5,143,679 A | 9/1992 | Weber |
| 5,151,092 A | 9/1992 | Buell |
| 5,156,793 A | 10/1992 | Buell |
| 5,167,897 A | 12/1992 | Weber |
| 5,192,606 A | 3/1993 | Proxmire |
| 5,221,274 A | 6/1993 | Buell |
| 5,242,436 A | 9/1993 | Weil |
| 5,246,433 A | 9/1993 | Hasse |
| 5,267,992 A | 12/1993 | Van Tilburg |
| 5,308,345 A | 5/1994 | Herrin |
| 5,360,420 A | 11/1994 | Cook |
| 5,407,507 A | 4/1995 | Ball |
| 5,422,172 A | 6/1995 | Wu |
| 5,518,801 A | 5/1996 | Chappell et al. |
| 5,540,796 A | 7/1996 | Fries |
| 5,562,646 A | 10/1996 | Goldman |
| 5,569,234 A | 10/1996 | Buell |
| 5,571,096 A | 11/1996 | Dobrin |
| 5,575,783 A | 11/1996 | Clear |
| 5,599,335 A | 2/1997 | Goldman |
| 5,628,097 A | 5/1997 | Benson |
| 5,643,588 A | 7/1997 | Roe |
| 5,669,894 A | 9/1997 | Goldman |
| 5,674,216 A | 10/1997 | Buell |
| 5,693,037 A | 12/1997 | Lee et al. |
| 5,700,255 A | 12/1997 | Curro |
| 5,702,551 A | 12/1997 | Huber |
| 5,735,840 A | 4/1998 | Kline |
| 5,827,259 A | 10/1998 | Laux |
| 5,897,545 A | 4/1999 | Kline |
| 5,904,675 A | 5/1999 | Laux |
| 5,916,661 A | 6/1999 | Benson |
| 5,928,212 A | 7/1999 | Kline |
| 5,957,908 A | 9/1999 | Kline |
| 5,961,997 A | 10/1999 | Swinehart |
| 5,968,025 A | 10/1999 | Roe |
| 5,993,433 A | 11/1999 | St. Louis |
| 6,004,893 A | 12/1999 | Van Tilburg |
| 6,010,491 A | 1/2000 | Roe et al. |
| 6,036,796 A | 3/2000 | Halbert |
| 6,051,094 A | 4/2000 | Melbye et al. |
| 6,107,537 A | 8/2000 | Elder |
| 6,107,539 A | 8/2000 | Palumbo |
| 6,118,041 A | 9/2000 | Roe |
| 6,120,487 A | 9/2000 | Ashton |
| 6,120,489 A | 9/2000 | Johnson |
| 6,149,934 A | 11/2000 | Krzysik et al. |
| 6,153,209 A | 11/2000 | Vega |
| 6,156,023 A | 12/2000 | Yoshioka |
| 6,238,683 B1 | 5/2001 | Burnett et al. |
| 6,248,097 B1 | 6/2001 | Beitz et al. |
| 6,248,195 B1 | 6/2001 | Schmitz |
| 6,251,097 B1 | 6/2001 | Kline |
| 6,369,290 B1 | 4/2002 | Glaug |
| 6,409,883 B1 | 6/2002 | Makolin |
| 6,410,129 B2 | 6/2002 | Zhang |
| 6,426,444 B2 | 7/2002 | Roe |
| 6,432,098 B1 | 8/2002 | Kline |
| 6,454,095 B1 | 9/2002 | Brisebois |
| 6,506,185 B1 | 1/2003 | Sauer et al. |
| 6,508,641 B1 | 1/2003 | Kubik |
| 6,545,197 B1 | 4/2003 | Muller |
| 6,568,530 B2 | 5/2003 | Takahashi |
| 6,572,595 B1 | 6/2003 | Klemp |
| 6,586,652 B1 | 7/2003 | Roe |
| 6,601,705 B2 | 8/2003 | Molina |
| 6,617,016 B2 | 9/2003 | Zhang |
| 6,627,787 B1 | 9/2003 | Roe |
| 6,645,330 B2 | 11/2003 | Pargass |
| 6,648,864 B2 | 11/2003 | Ronn |
| 6,669,618 B2 | 12/2003 | Reising |
| 6,699,228 B1 | 3/2004 | Chmielewski et al. |
| 6,790,798 B1 | 9/2004 | Suzuki |
| 6,825,393 B2 | 11/2004 | Roe |
| 6,830,800 B2 | 12/2004 | Curro et al. |
| 6,861,571 B1 | 3/2005 | Roe |
| 7,087,287 B2 | 8/2006 | Curro et al. |
| 7,371,302 B2 | 5/2008 | Miyamoto et al. |
| 7,569,039 B2 | 8/2009 | Matsuda |
| 7,785,309 B2 | 8/2010 | Van Gompel et al. |
| 7,803,244 B2 | 9/2010 | Siqueira et al. |
| 7,824,594 B2 | 11/2010 | Qureshi |
| 7,896,641 B2 | 3/2011 | Qureshi |
| 8,062,572 B2 | 11/2011 | Qureshi |
| 8,071,990 B2 | 12/2011 | Bogner et al. |
| 8,118,801 B2 | 2/2012 | Macura |
| 8,186,296 B2 | 5/2012 | Brown |
| 8,257,333 B2 | 9/2012 | Hancock-cooke et al. |
| 8,395,012 B2 | 3/2013 | Bacon et al. |
| 8,496,638 B2 | 7/2013 | Lord et al. |
| 8,608,720 B2 | 12/2013 | Erickson et al. |
| 8,662,706 B2 | 3/2014 | Komatsu |
| 8,715,464 B2 | 5/2014 | Young et al. |
| 8,778,127 B2 | 7/2014 | Schneider |
| 8,936,697 B2 | 1/2015 | Scharpf et al. |
| 8,950,912 B2 | 2/2015 | Chen |
| 8,956,493 B2 | 2/2015 | Tenorio et al. |
| 9,005,392 B2 | 4/2015 | Schneider |
| 9,248,054 B2 | 2/2016 | Brown |
| 9,265,672 B2 | 2/2016 | Brown |
| 9,283,124 B2 | 3/2016 | Hashimoto et al. |
| 9,295,590 B2 | 3/2016 | Brown |
| 9,429,304 B2 | 8/2016 | Masuda et al. |
| 9,464,777 B2 | 10/2016 | Boyce |
| 9,468,569 B2 | 10/2016 | Hancock-cooke et al. |
| 9,687,580 B2 | 6/2017 | Schonbeck |
| 9,913,871 B2 | 3/2018 | Ellington et al. |
| 9,962,297 B2 | 5/2018 | Eckstein et al. |
| 10,052,237 B2 | 8/2018 | Galie et al. |
| 10,159,610 B2 | 12/2018 | Barnes |
| 10,470,943 B2 | 11/2019 | Jang |

(56) References Cited

U.S. PATENT DOCUMENTS

| | | |
|---|---|---|
| 11,096,836 B2 | 8/2021 | Bishop et al. |
| 11,369,526 B2 | 6/2022 | Matsui et al. |
| 11,554,055 B2 | 1/2023 | Bishop et al. |
| 2002/0064639 A1 | 5/2002 | Rearick et al. |
| 2002/0129740 A1 | 9/2002 | Kato et al. |
| 2002/0165170 A1 | 11/2002 | Wilson et al. |
| 2002/0173768 A1* | 11/2002 | Elsberg ............... A61F 13/5655 604/387 |
| 2003/0121380 A1 | 7/2003 | Cowell |
| 2003/0154904 A1 | 8/2003 | Klofta et al. |
| 2003/0187414 A1 | 10/2003 | Reiss et al. |
| 2003/0233082 A1 | 12/2003 | Kline |
| 2004/0097895 A1 | 5/2004 | Busam |
| 2004/0122413 A1 | 6/2004 | Roessler |
| 2004/0158212 A1 | 8/2004 | Ponomarenko |
| 2004/0196734 A1 | 10/2004 | Mehta et al. |
| 2005/0096616 A1 | 5/2005 | Arora et al. |
| 2005/0107764 A1 | 5/2005 | Matsuda |
| 2005/0171498 A1 | 8/2005 | Reiss et al. |
| 2005/0217812 A1 | 10/2005 | Stoyanov et al. |
| 2006/0094320 A1 | 5/2006 | Chen et al. |
| 2006/0129115 A1 | 6/2006 | Visscher |
| 2006/0167434 A1 | 7/2006 | Ashton et al. |
| 2006/0196796 A1 | 9/2006 | Motsch et al. |
| 2006/0264862 A1 | 11/2006 | Yoshida et al. |
| 2006/0264863 A1 | 11/2006 | Blyth |
| 2006/0287637 A1 | 12/2006 | Lam |
| 2007/0032772 A1 | 2/2007 | Ehrnsperger |
| 2007/0078427 A1 | 4/2007 | Raycheck |
| 2007/0093769 A1 | 4/2007 | Kline |
| 2007/0149937 A1 | 6/2007 | Reiss et al. |
| 2007/0219521 A1 | 9/2007 | Hird |
| 2007/0287980 A1 | 12/2007 | Kline et al. |
| 2008/0099360 A1 | 5/2008 | Smith |
| 2008/0250681 A1 | 10/2008 | Jackson |
| 2008/0269704 A1 | 10/2008 | Hansson et al. |
| 2009/0149827 A1 | 6/2009 | Mlinar et al. |
| 2009/0155325 A1 | 6/2009 | Magin et al. |
| 2009/0157034 A1 | 6/2009 | Mattingly et al. |
| 2009/0204090 A1 | 8/2009 | Dennis et al. |
| 2009/0294044 A1 | 12/2009 | Gill et al. |
| 2009/0312730 A1 | 12/2009 | Lavon |
| 2010/0181223 A1 | 7/2010 | Warren |
| 2010/0221496 A1 | 9/2010 | De Jong |
| 2010/0230857 A1 | 9/2010 | Muhs et al. |
| 2010/0305532 A1 | 12/2010 | Ashton et al. |
| 2011/0040273 A1 | 2/2011 | Sablone |
| 2011/0046594 A1 | 2/2011 | Sablone |
| 2011/0073513 A1 | 3/2011 | Weisman et al. |
| 2011/0139657 A1 | 6/2011 | Hird |
| 2011/0139658 A1 | 6/2011 | Hird |
| 2011/0139659 A1 | 6/2011 | Hird |
| 2011/0139662 A1 | 6/2011 | Hird |
| 2011/0152812 A1 | 6/2011 | Hird |
| 2011/0215017 A1 | 9/2011 | Coulter et al. |
| 2011/0315585 A1 | 12/2011 | Meyer et al. |
| 2011/0319849 A1 | 12/2011 | Collias et al. |
| 2012/0061015 A1 | 3/2012 | Lavon |
| 2012/0061016 A1 | 3/2012 | Lavon |
| 2012/0143165 A1 | 6/2012 | Macura |
| 2012/0206265 A1 | 8/2012 | Solazzo et al. |
| 2012/0276341 A1 | 11/2012 | Lake |
| 2012/0277703 A1 | 11/2012 | Rhein |
| 2012/0277713 A1 | 11/2012 | Raycheck |
| 2013/0018339 A1 | 1/2013 | Kaiser et al. |
| 2013/0072887 A1 | 3/2013 | Lavon |
| 2013/0126071 A1 | 5/2013 | Shin et al. |
| 2013/0211356 A1 | 8/2013 | Nishikawa |
| 2013/0255861 A1 | 10/2013 | Schneider |
| 2013/0255862 A1 | 10/2013 | Schneider |
| 2013/0255863 A1 | 10/2013 | Lavon |
| 2013/0255864 A1 | 10/2013 | Schneider |
| 2013/0255865 A1 | 10/2013 | Brown |
| 2013/0274697 A1 | 10/2013 | Godlewski |
| 2013/0306226 A1 | 11/2013 | Zink |
| 2013/0313149 A1 | 11/2013 | Hird et al. |
| 2014/0005621 A1 | 1/2014 | Roe |
| 2014/0039422 A1 | 2/2014 | Scott |
| 2014/0079919 A1 | 3/2014 | Bunnelle |
| 2014/0093697 A1 | 4/2014 | Perry et al. |
| 2014/0148773 A1 | 5/2014 | Brown |
| 2014/0272370 A1 | 9/2014 | Broyles |
| 2014/0276512 A1 | 9/2014 | Cheng et al. |
| 2014/0350504 A1 | 11/2014 | Coenen |
| 2014/0352090 A1 | 12/2014 | Schuchter |
| 2014/0371700 A1 | 12/2014 | Patel et al. |
| 2015/0283003 A1 | 10/2015 | Rosati |
| 2015/0366724 A1 | 12/2015 | Fukuzawa et al. |
| 2015/0374561 A1 | 12/2015 | Hubbard, Jr. et al. |
| 2016/0101003 A1 | 4/2016 | Jennewein et al. |
| 2016/0206774 A1 | 7/2016 | Hird |
| 2016/0270973 A1 | 9/2016 | Surushe et al. |
| 2016/0270979 A1 | 9/2016 | Raycheck et al. |
| 2016/0270980 A1 | 9/2016 | Raycheck et al. |
| 2016/0350828 A1 | 12/2016 | Schmidt et al. |
| 2017/0000658 A1 | 1/2017 | Chatterjee |
| 2017/0056253 A1 | 3/2017 | Chester et al. |
| 2017/0246052 A1 | 8/2017 | Ludwig |
| 2017/0252229 A1 | 9/2017 | Bonelli |
| 2017/0290712 A1 | 10/2017 | Findley |
| 2017/0296399 A1 | 10/2017 | Kline et al. |
| 2017/0313034 A1 | 11/2017 | Takeda et al. |
| 2017/0319399 A1 | 11/2017 | Desai et al. |
| 2017/0333261 A1 | 11/2017 | Chatterjee |
| 2017/0333262 A1 | 11/2017 | Chatterjee et al. |
| 2018/0042777 A1 | 2/2018 | Dalal |
| 2018/0042778 A1 | 2/2018 | Lenser |
| 2018/0042779 A1 | 2/2018 | Lenser et al. |
| 2018/0042780 A1 | 2/2018 | Lenser et al. |
| 2018/0042785 A1 | 2/2018 | Dalal |
| 2018/0042786 A1 | 2/2018 | Mueller et al. |
| 2018/0042787 A1 | 2/2018 | Lenser et al. |
| 2018/0055698 A1 | 3/2018 | Bishop et al. |
| 2018/0071155 A1 | 3/2018 | Bishop |
| 2018/0140469 A1 | 5/2018 | Kane et al. |
| 2018/0169964 A1 | 6/2018 | Schneider |
| 2018/0199743 A1 | 7/2018 | Kajak |
| 2018/0250171 A1 | 9/2018 | Bäck et al. |
| 2018/0256419 A1 | 9/2018 | Mcgilloway et al. |
| 2018/0271716 A1 | 9/2018 | Dalal |
| 2018/0360739 A1 | 12/2018 | Lorenz et al. |
| 2018/0369091 A1 | 12/2018 | Avshalomov |
| 2019/0010258 A1 | 1/2019 | Mitchell et al. |
| 2019/0070042 A1 | 3/2019 | Beck |
| 2019/0083325 A1 | 3/2019 | Mccormick |
| 2019/0083331 A1 | 3/2019 | Barnes |
| 2019/0175417 A1 | 6/2019 | Graham |
| 2020/0038256 A1 | 2/2020 | Jang et al. |
| 2020/0054496 A1 | 2/2020 | Mccormick et al. |
| 2020/0054497 A1 | 2/2020 | Mccormick et al. |
| 2020/0078230 A1 | 3/2020 | Mccormick et al. |
| 2020/0093652 A1 | 3/2020 | Mccormick et al. |
| 2020/0093653 A1 | 3/2020 | Mccormick et al. |
| 2020/0121519 A1 | 4/2020 | Mccormick et al. |
| 2020/0155372 A1 | 5/2020 | Kleuskens et al. |
| 2020/0163812 A1 | 5/2020 | Zuleger et al. |
| 2020/0197560 A1 | 6/2020 | Buchalter |
| 2020/0375807 A1 | 12/2020 | Schneider et al. |
| 2020/0375815 A1 | 12/2020 | Raycheck et al. |
| 2020/0375816 A1 | 12/2020 | Mccormick et al. |
| 2021/0128366 A1 | 5/2021 | Schneider et al. |
| 2021/0128369 A1 | 5/2021 | Raycheck et al. |
| 2021/0346211 A1 | 11/2021 | Kilbacak et al. |
| 2024/0415706 A1 | 12/2024 | Schneider et al. |

FOREIGN PATENT DOCUMENTS

| | | |
|---|---|---|
| CN | 1328438 A | 12/2001 |
| CN | 101327156 A | 12/2008 |
| CN | 101389237 A | 3/2009 |
| CN | 104244881 A | 12/2014 |
| CN | 106038076 A | 10/2016 |
| CN | 106236389 A | 12/2016 |
| CN | 106456410 A | 2/2017 |

(56) References Cited

FOREIGN PATENT DOCUMENTS

| | | | |
|---|---|---|---|
| CN | 107405227 A | 11/2017 |
| CN | 107809989 A | 3/2018 |
| CN | 107820419 A | 3/2018 |
| CN | 108472171 A | 8/2018 |
| CN | 109069313 A | 12/2018 |
| CN | 109069315 A | 12/2018 |
| CN | 109475452 A | 3/2019 |
| CN | 109843242 A | 6/2019 |
| CN | 114025727 A | 2/2022 |
| EP | 2260813 B1 | 7/2015 |
| JP | S63211303 A | 9/1988 |
| JP | 2001095838 A | 4/2001 |
| JP | 2002232009 A | 8/2002 |
| JP | 2002541918 A | 12/2002 |
| JP | 2008074327 A | 4/2008 |
| JP | 2008113684 A | 5/2008 |
| JP | 2008113685 A | 5/2008 |
| JP | 2010269029 A | 12/2010 |
| JP | 2011010822 A | 1/2011 |
| JP | 2011062226 A | 3/2011 |
| JP | 2012243462 A | 12/2012 |
| JP | 2013164937 A | 8/2013 |
| JP | 2013168434 A | 8/2013 |
| JP | 2013180171 A | 9/2013 |
| JP | 2016112341 A | 6/2016 |
| JP | 2016182169 A | 10/2016 |
| JP | 2017060635 A | 3/2017 |
| RU | 24771 U1 | 8/2002 |
| WO | 9511650 A1 | 5/1995 |
| WO | 9524173 A2 | 9/1995 |
| WO | 9720532 A1 | 6/1997 |
| WO | 2007106929 A1 | 9/2007 |
| WO | 2009012284 A1 | 1/2009 |
| WO | 2013002691 A1 | 1/2013 |
| WO | 2013173291 A1 | 11/2013 |
| WO | 2014103464 A1 | 7/2014 |
| WO | 2016023016 A1 | 2/2016 |
| WO | 2017118612 A1 | 7/2017 |
| WO | 2017124092 A1 | 7/2017 |
| WO | 2018089088 A1 | 5/2018 |
| WO | 2020003160 A2 | 1/2020 |
| WO | 2020004476 A1 | 1/2020 |
| WO | 2020004499 A1 | 1/2020 |
| WO | 2020115916 A1 | 6/2020 |
| WO | 2020116554 A1 | 6/2020 |
| WO | 2020116592 A1 | 6/2020 |
| WO | 2020116593 A1 | 6/2020 |
| WO | 2020116595 A1 | 6/2020 |

OTHER PUBLICATIONS

Unpublished U.S. Appl. No. 18/493,083, filed Oct. 24, 2023, to Jeromy Thomas Raycheck et al.
"Surround." Merriam-Webster.com Dictionary, Merriam-Webster, https://www.merriam-webster.com/dictionary/surround. Accessed Jun. 15, 2021, 8 Pages.
Epsilon, Water Soluble Dyes/Solvent Green 7 and Corresponding Material Safety Data Sheet , Jul. 15, 2013, 5 pages.
PCT Search Report and Written Opinion for PCT/US2021/029512 dated Sep. 7, 2021, 12 pages.
All Office Actions, U.S. Appl. No. 16/864,267, filed May 1, 2020.
All Office Actions, U.S. Appl. No. 16/864,292, filed May 1, 2020.
All Office Actions, U.S. Appl. No. 16/885,622, filed May 28, 2020.
All Office Actions, U.S. Appl. No. 17/029,211, filed Sep. 23, 2020.
All Office Actions, U.S. Appl. No. 17/029,486, filed Sep. 23, 2020.
All Office Actions; U.S. Appl. No. 17/307,291, filed May 4, 2021.
All Office Actions; U.S. Appl. No. 18/815,950, filed Aug. 27, 2024.

* cited by examiner

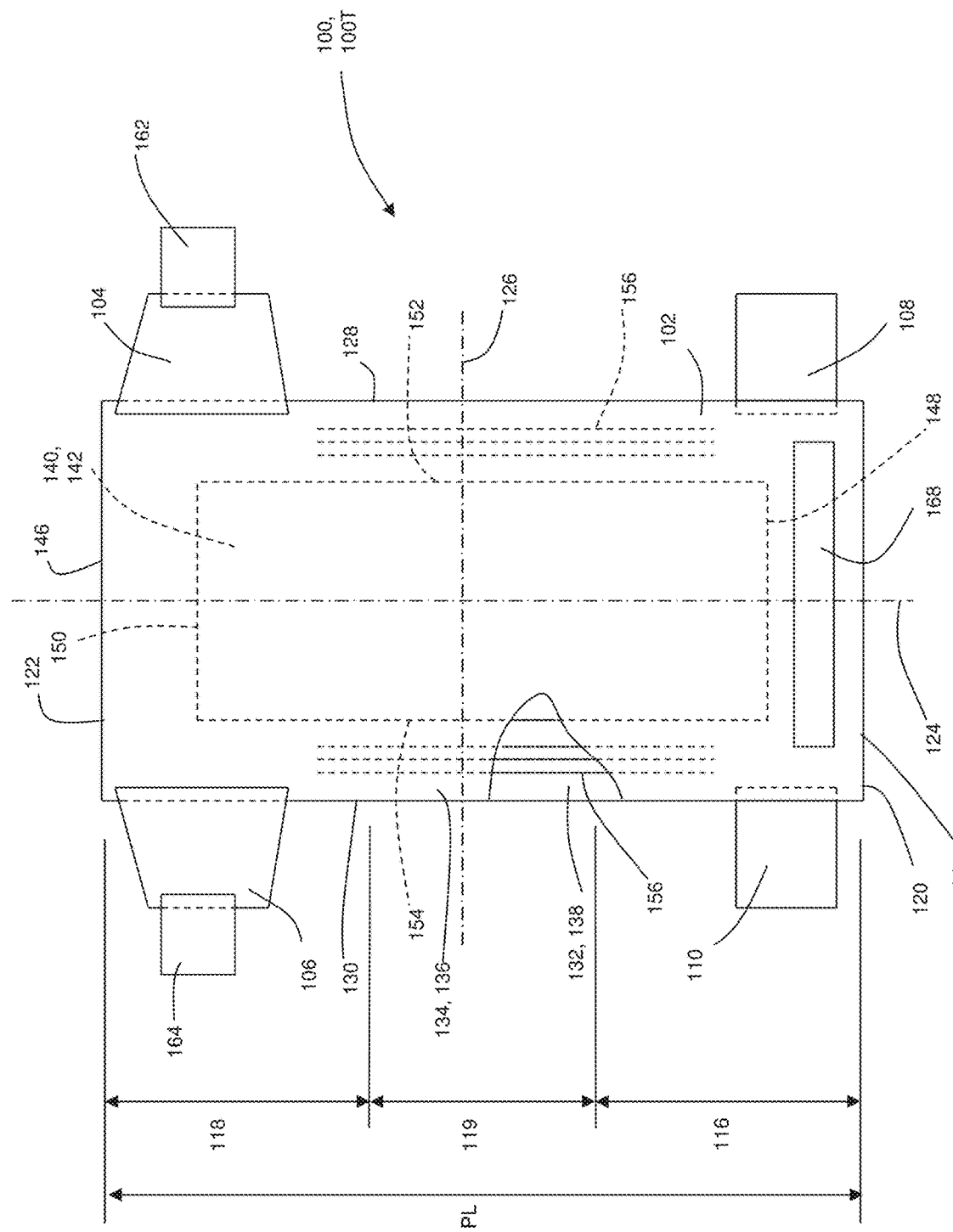

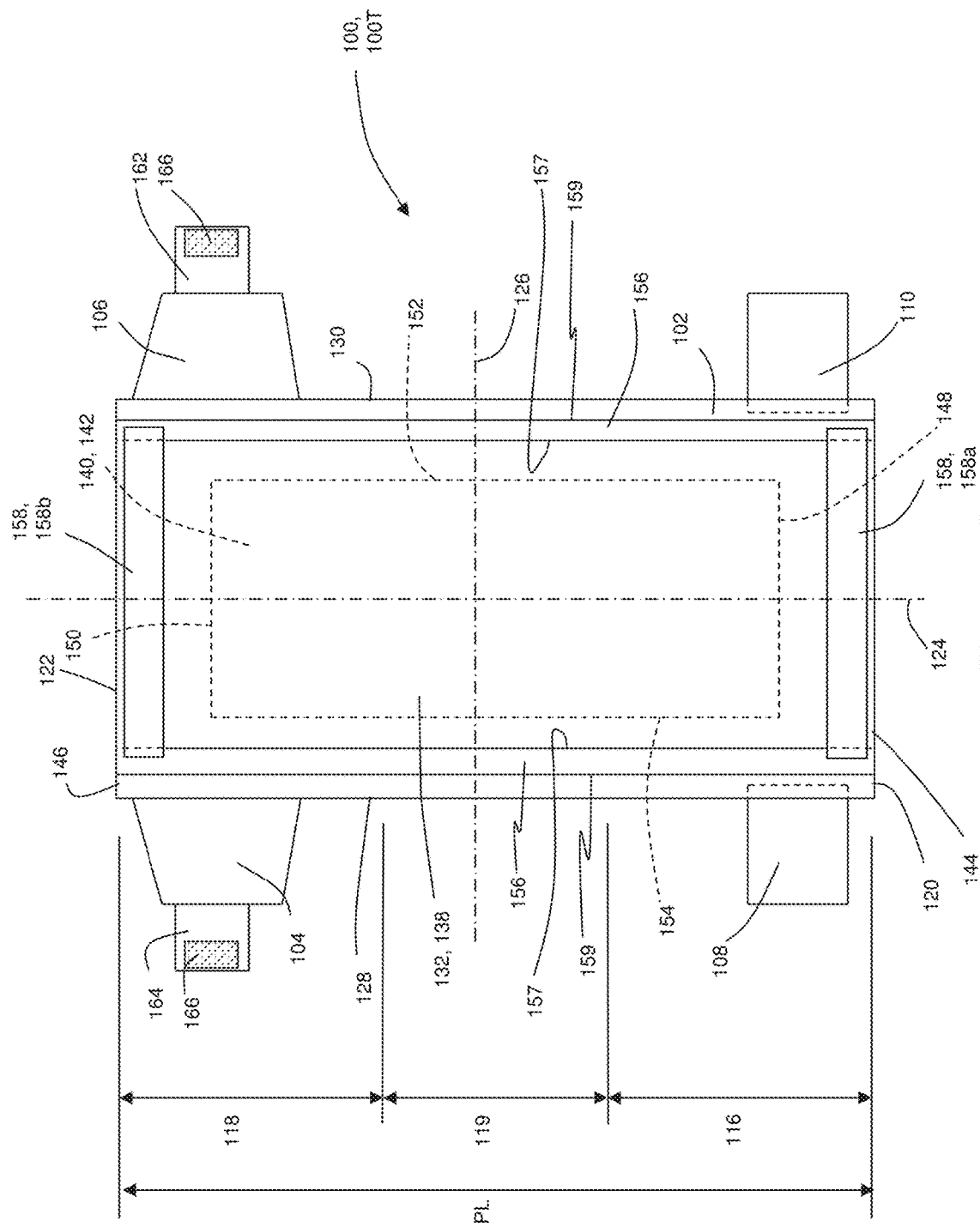

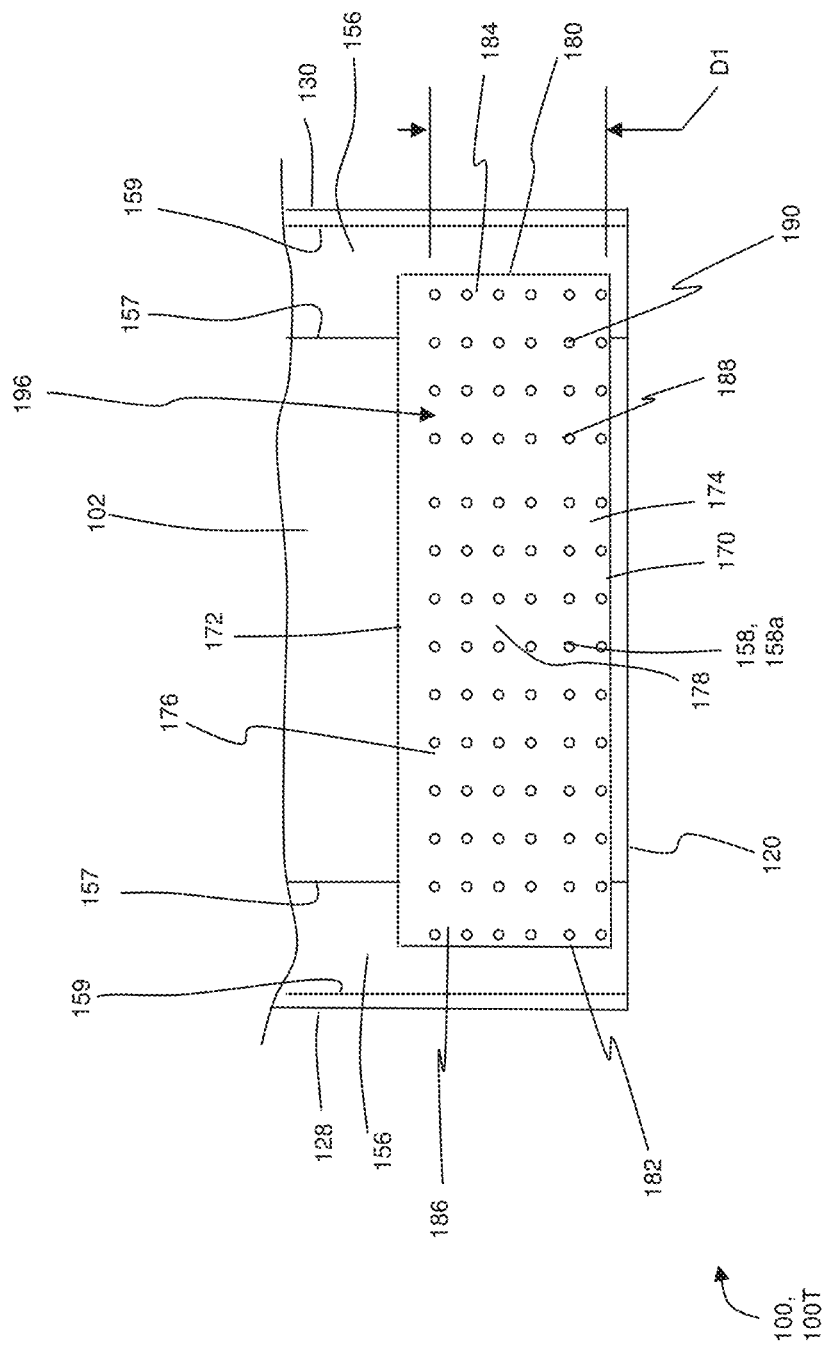

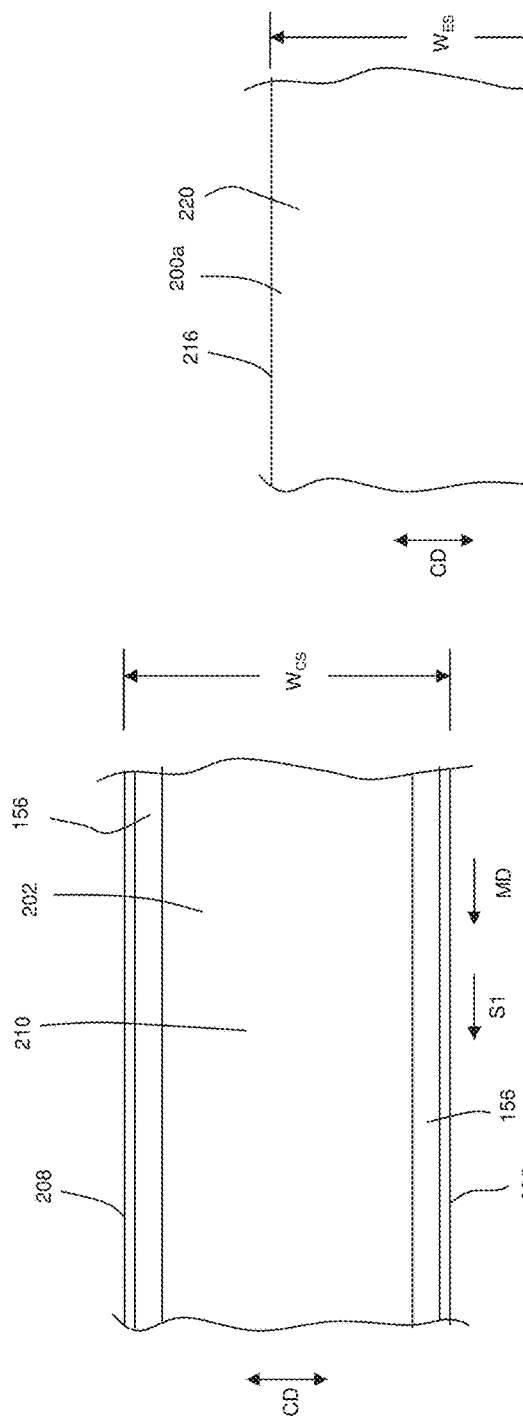
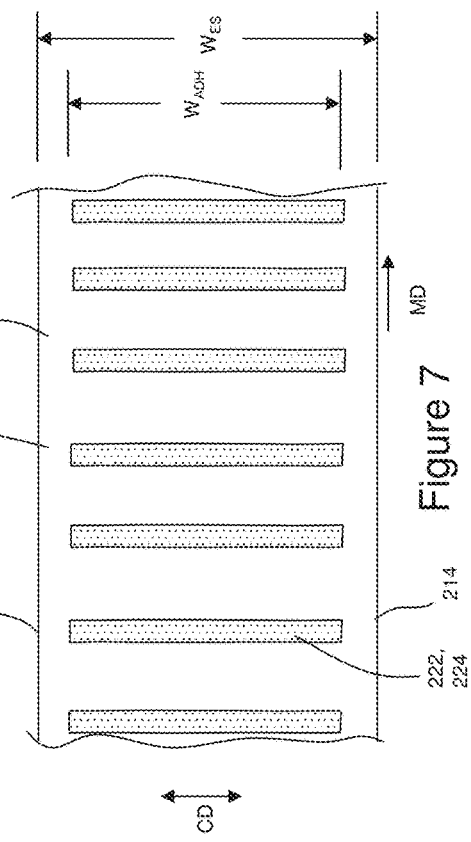

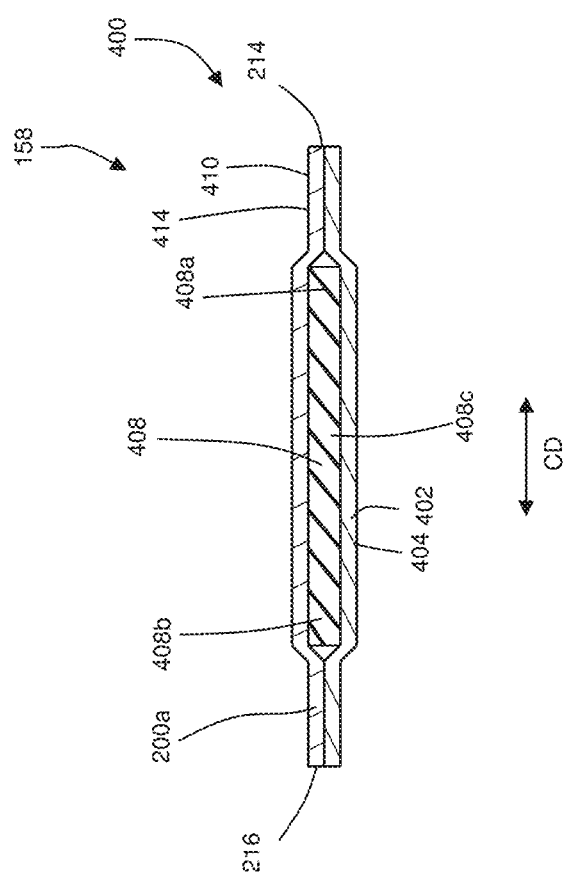
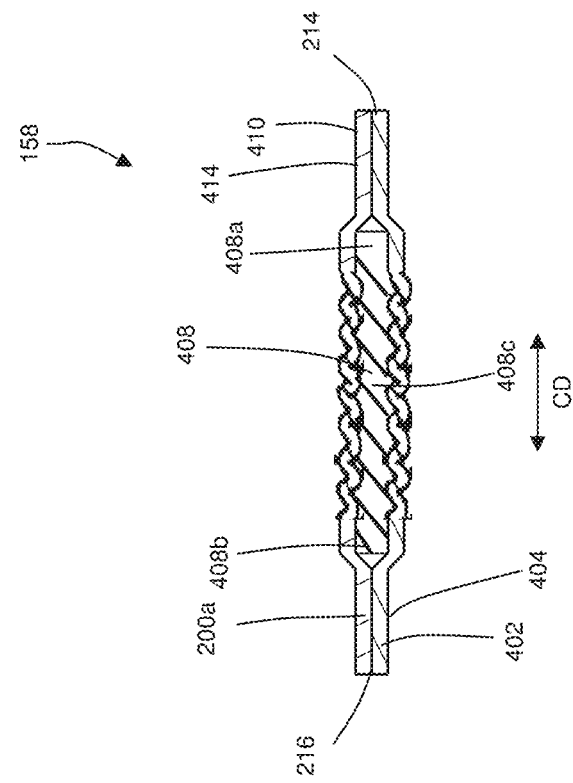

ABSORBENT ARTICLES INCLUDING FRONT AND BACK WAIST PANELS WITH DIFFERENT STRETCH CHARACTERISTICS

CROSS REFERENCE TO RELATED APPLICATION

This application claims the benefit of U.S. Provisional Application No. 63/020,043, filed May 5, 2020, which is incorporated herein by reference.

FIELD OF THE INVENTION

The present disclosure relates to absorbent articles including waist panels, and more particularly, to front and back waist panels with different stretch characteristics.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and parts such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles, such as diapers, have components that include elastic parts, such as for example, waistbands. In some configurations, waistbands may be provided as a single layer of elastic material, such as an elastic film. In some configurations, the waistbands may be provided as an elastic laminate that may include elastic material bonded to one or more substrates such as nonwovens, wherein the elastic material may include an elastic film and/or elastic strands. In some assembly operations, the waistbands are joined to an advancing carrier web, such as a continuous topsheet or backsheet web, while the waistbands are in a stretched condition. As such, when the waistbands relax, the carrier web gathers to form corrugations. The resulting laminate is stretchable to the extent that the corrugations allow the waistband to elongate.

When manufacturing diapers, the waistband may be provided as a continuous length of waistband material that may be stretched; cut into discrete waistbands; and bonded with the advancing carrier web, such as a continuous topsheet or backsheet web, while the waistband is in a stretched state. With some diapers, it may be desirable to include a front waistband in a front waist region and a back waistband in an opposing back waist region. Some assembly operations may apply a piece of waistband material to the advancing carrier web that is subsequently cut into separate front and back waistbands when the advancing carrier web is subject to the final knife cut that separates the carrier web into discrete diapers. In turn, the front and back waistbands may be created from the same continuous length of waistband material.

In some configurations, it may be desirable to provide diapers with front and rear waistbands having different stretch characteristics to help improve fit, comfort, and/or performance. In order to accommodate such a requirement, manufacturing operations may require front and back waistbands to be created from different supplies of waistband materials that have been pre-made with different stretch characteristics. However, requiring different supplies of waistband materials may result in increased manufacturing costs and complexities.

Consequently, it would be beneficial to provide absorbent articles with front and back waist features having different stretch characteristics resulting from different structural and/or morphological features, wherein such features may be imparted to a single source stretch laminate during the absorbent article assembly process.

SUMMARY OF THE INVENTION

In one form, an absorbent article comprises: a first waist region, a second waist region, and a crotch region disposed between the front and second waist regions; a first waist edge, a second waist edge, a first longitudinal side edge; and a second longitudinal edge; a chassis comprising a topsheet, a backsheet, and an absorbent core positioned between the topsheet and the backsheet; leg gasketing elements extending from the first waist region to the second waist region; a first waist panel comprising an inboard lateral edge, an outboard lateral edge, and two longitudinal edges, the first waist panel comprising a first elastic film bonded to a first nonwoven in a stretched state, and wherein the first waist panel is connected with the chassis and positioned in the first waist region; a second waist panel comprising an inboard lateral edge, an outboard lateral edge, and two longitudinal edges, the second waist panel comprising a second elastic film bonded to a second nonwoven in a stretched state, and wherein the second waist panel is connected with the chassis and positioned in the second waist region; and wherein the first waist panel comprises a first structural feature that is not included in the second waist panel or is different from a second structural feature included in the second waist panel, wherein the first structural feature or the second structural feature provides different stretch characteristics between the first waist panel and the second waist panel.

In another form, an absorbent article comprises: a first waist region, a second waist region, and a crotch region disposed between the first and second waist regions; a first waist edge, a second waist edge, a first longitudinal side edge; and a second longitudinal edge; a chassis comprising a topsheet, a backsheet, and an absorbent core positioned between the topsheet and the backsheet; leg gasketing elements extending from the first waist region to the second waist region; a first waist panel positioned in the first waist region, the first waist panel comprising an inboard lateral edge, an outboard lateral edge, and two longitudinal edges, and wherein a region of the first waist panel extending along the longitudinal edges are mechanically bonded to the chassis; and a second waist panel positioned in the second waist region, the second waist panel comprising an inboard lateral edge, an outboard lateral edge, and two longitudinal edges, the second waist panel comprising an elastic film bonded to a nonwoven in a stretched state, and wherein regions of the second waist panel extending along the outboard lateral edge and regions extending along the longitudinal edges are bonded to the chassis in the second waist region, and at least a portion of the inboard lateral edge of the second waist panel is unattached to the chassis.

In yet another form, an absorbent article comprises: a front waist region, a back waist region, and a crotch region disposed between the front and back waist regions; a front waist edge, a back waist edge, a first longitudinal side edge; and a second longitudinal edge; a chassis comprising a topsheet, a backsheet, and an absorbent core positioned between the topsheet and the backsheet; leg gasketing elements extending from the first waist region to the second waist region;

a first waist panel comprising an inboard lateral edge, an outboard lateral edge, and two longitudinal edges, the first waist panel comprising a first elastic film bonded to a first nonwoven in a stretched state and positioned in the front waist region; a second waist panel comprising an inboard lateral edge, an outboard lateral edge, and two longitudinal edges, the second waist panel comprising a second elastic film bonded to a second nonwoven in a stretched state, and wherein the second waist panel is connected with the chassis and positioned in the back waist region; and wherein the first pressure bonds define first stretch characteristics of the first waist panel, and wherein the second pressure bonds define second stretch characteristics of the second waist panel that are different from the first stretch characteristics.

In still another form, a method of providing an absorbent article having a first elastic waist panel and a second elastic waist panel, the first and second elastic waist panels comprising different stretch characteristics, comprises steps of: providing a continuous length of chassis; applying a first elastic waist panel and a second elastic waist panel to the continuous length of chassis; creating a morphological difference between the first waist panel and the second waist panel; and separating the continuous length of chassis into individual absorbent articles.

BRIEF DESCRIPTION OF THE DRAWINGS

FIG. 1A is a partially cut away plan view of an absorbent article in the form of a taped diaper that may include one or more substrates assembled in accordance with the present disclosure with the portion of the diaper that faces away from a wearer oriented towards the viewer.

FIG. 1B is a plan view of the absorbent article of FIG. 1A that may include one or more substrates assembled in accordance with the present disclosure with the portion of the diaper that faces toward a wearer oriented towards the viewer.

FIG. 2C is a detailed view of the first waist panel from FIG. 2 illustrating a structural feature configuration with pressure bonds.

FIG. 5A is a view of a carrier substrate with leg cuffs taken along section 5-5 in FIG. 4.

FIG. 6 is a view of a continuous elastic substrate taken along section 6-6 in FIG. 4.

FIG. 7 is a view of a continuous elastic substrate with discrete patches of adhesive taken along section 7-7 in FIG. 4.

FIG. 18 is a cross sectional view of the elastic substrate from FIG. 17A taken along line 18-18.

FIG. 19 is a cross-sectional view of the elastic substrate from FIG. 18 in a relaxed, contracted condition.

DETAILED DESCRIPTION OF THE INVENTION

Figure 2:
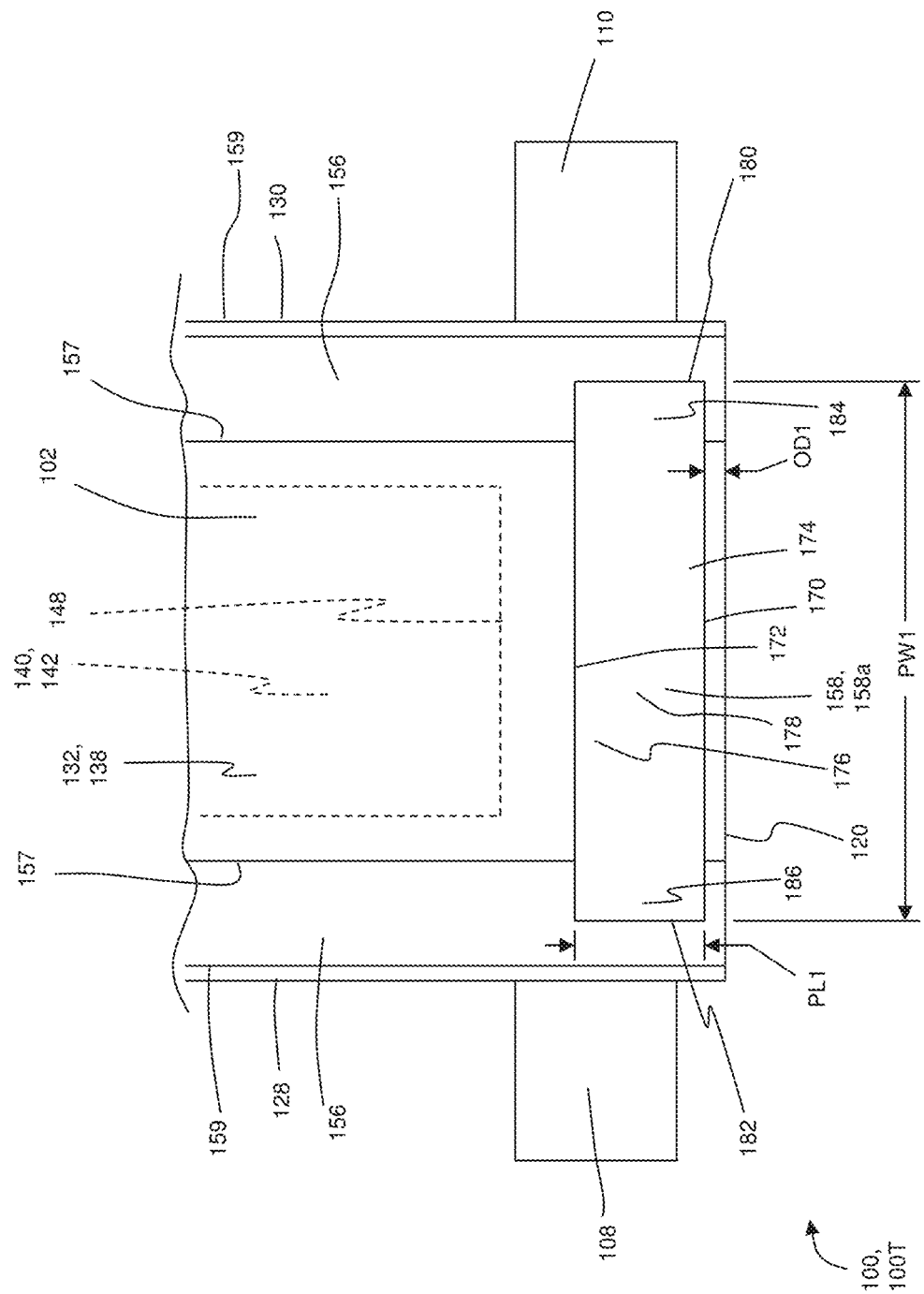
FIG. 2 is a detailed view of a first waist panel with the portion of the diaper that faces toward a wearer oriented towards the viewer.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

"Consolidation," "consolidating," and "consolidated" refers to a material undergoing a reduction in elongation from a first stretched length to a second stretched length that is less than the first stretched length and greater than zero.

"Relaxed state" defines a length of material when not stretched by an applied force.

In the context of the present description, an elongation of 0% refers to a material in relaxed state having a relaxed length of L, and elongation of 150% represents 2.5× the relaxed length, L, of the material. For example, an elastic film having a relaxed length of 100 millimeters would have a length of 250 millimeters at 150% elongation. And an elastic film having a relaxed length of 100 millimeters would have a length of 180 millimeters at 80% elongation.

In the context of the present description, a contraction of 60% represents 0.6× contraction of an initial stretch length, L, of a material. For example, an elastic film having an initial stretch length of 250 millimeters would have a contracted length of 100 millimeters at 60% contraction. And an elastic film having an initial stretch length of 180 millimeters would have a length of 100 millimeters at 44% contraction.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the methods herein. For example, some nonwovens may have a basis weight of at least about 8 gsm, 12 gsm, 16 gsm, 20 gsm, 25 gsm, 30 gsm, 40 gsm, or 65 gsm. Some nonwovens may have basis weight of about 8 gsm to about 65 gsm, specifically reciting all 1 gsm increments within the above-recited ranges and all ranges formed therein or thereby.

It is to be appreciated that films having various basis weights can be used in accordance with the methods herein. For example, some films may have a basis weight of at least about 8 gsm, 12 gsm, 16 gsm, 20 gsm, 25 gsm, 30 gsm, 40 gsm, or 60 gsm. Some films may have basis weight of about 5 gsm to about 150 gsm, specifically reciting all 1 gsm increments within the above-recited ranges and all ranges formed therein or thereby.

It is to be appreciated that elastic films discussed herein may comprise various materials and/or components. Some elastomeric compositions may comprise thermoplastic elastomers selected from the group consisting of Styrenic block copolymers, poly-esters, polyurethanes, polyether amides, and combinations thereof. Suitable styrenic block copolymers may be diblock, triblock, tetrablock, or other multi-block copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON (styrenic block copolymer; available from the Kraton Chemical Company, Houston, TX), SEPTON (styrenic block copolymer; available from Kuraray America, Inc., New York, NY), VECTOR (styrenic block copolymer; available from TSRC Dexco Chemical Company, Houston, TX) can be used. Additional commercially available elastomers include ESTANE (polyurethane; available from Lubrizol, Inc, Ohio), PEBAX (polyether block amide; available from Arkema Chemicals, Philadelphia, PA), and HYTREL (polyester; available from DuPont, Wilmington, DE).

Semi-crystalline, or metallocene polyolefins may be used in disposable absorbent products. The polyolefin elastomer materials herein may include, but are not limited to, any polymers or copolymers of polyolefins such as polyethylene and polypropylene. Examples of elastomeric polypropylenes include an elastic random poly(propylene/olefin) copolymer, an isotactic polypropylene containing stereo-irregularity, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and blends or combinations thereof. Some homopolyolefins and random copolymers, as well as blends of such random copolymers, known by tradenames Vistamaxx™ available from ExxonMobil and VERSIFY™ from Dow, tend to show elastic performance. In some embodiments, two or more elastomers may be blended to achieve the desired elastic performance. For example, Styrenic block copolymer can be blended with polyolefin based elastomers, or polypropylene based elastomer can be blended with other polyolefin based elastomers.

Components of the disposable absorbent articles (i.e., diaper, disposable pant, adult incontinence article, sanitary napkin, pantiliner, etc.) described in this specification can at least partially be comprised of bio-sourced content as described in US 2007/0219521 A1 Hird et al published on Sep. 20, 2007, US 2011/0139658 A1 Hird et al published on Jun. 16, 2011, US 2011/0139657 A1 Hird et al published on Jun. 16, 2011, US 2011/0152812 A1 Hird et al published on Jun. 23, 2011, US 2011/0139662 A1 Hird et al published on Jun. 16, 2011, and US 2011/0139659 A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases. In at least one embodiment, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B. In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Aspects of the present disclosure relate to absorbent articles with front and back waist panels having different stretch characteristics. As discussed below, absorbent article may comprise: a first waist region, a second waist region, and a crotch region disposed between the front and second waist regions. The absorbent article may also comprise a chassis comprising a topsheet, a backsheet, and an absorbent core positioned between the topsheet and the backsheet. A first waist panel may be connected with the chassis and positioned in the first waist region, and a second waist panel may be connected with the chassis and positioned in the second waist region. In some configurations, the first waist panel may comprise a first structural feature that is not included in the second waist panel or may comprise a first structural feature is different from a second structural feature included in the second waist panel. As such, the first structural feature provides different stretch characteristics between the first waist panel and the second waist panel. Examples of first and/or second structural features may include: embossing, apertures, slits, melted material, compressed material, plastic deformation, folds, adhesive bonds, and/or pressure bonds. It is to be appreciated that such structural features may be formed in various ways, such as for example, by the application of folds, ultrasonic energy, pressure, and/or heat. The waist panels are discussed below in the context of absorbent articles that may be configured as taped diapers or pant diapers.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, which are all incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, which are all incorporated by reference herein.

For the purposes of a specific illustration, FIGS. 1A and 1B show an example of an absorbent article 100 that may be assembled in accordance with the present disclosure. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes an absorbent chassis 102, first and second rear side panels 104 and 106; and first and second front side panels 108 and 110.

As shown in FIGS. 1A and 1B, the absorbent article 100 and the chassis 102 each include a first waist region 116, a second waist region 118, and a crotch region 119 disposed intermediate the first and second waist regions. The first waist region 116 may be configured as a front waist region, and the second waist region 118 may be configured as a back waist region. In some embodiments, the length of each of the front waist region, back waist region, and crotch region may be ⅓ of the length of the absorbent article 100. The absorbent article 100 may also include a laterally extending first waist edge 120 in the first waist region 116, wherein the first waist edge 120 may be configured as a front waist edge. In addition, the absorbent article 100 may include a laterally extending second waist edge 122 in the second waist region 118, wherein the second waist edge 122 may be configured as a back waist edge. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the absorbent article 100 includes an inner, wearer facing surface 132, and an outer, garment facing surface 134. As such, it is also to be appreciated that the various components of the absorbent article described below may each include inner, wearer facing surfaces 132, and an outer, garment facing surfaces 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the absorbent article 100 may also include other features, such as leg gasketing elements, waist panels, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the absorbent article 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the absorbent article 100 may also be made laterally extensible. The additional extensibility may help allow the absorbent article 100 to conform to the body of a wearer during movement by the wearer. The additional extensibility may also help, for example, the user of the absorbent article 100, including a chassis 102 having a particular size before extension, to extend the front waist region 116, the back waist region 118, or both waist regions of the absorbent article 100 and/or chassis 102 to provide additional body coverage for wearers of differing size, i.e., to tailor the absorbent article to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the absorbent article 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the absorbent article 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet 136 may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the absorbent article 100.

Also described above, the absorbent article 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916, 661; 6,545,197; and 6,107,539, which are all incorporated by reference herein.

As mentioned above, the absorbent article 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the absorbent article. Exemplary absorbent structures for use as the absorbent core of the present disclosure are described in U.S. Pat. Nos. 4,610,678; 4,673,402; 4,888,231; and 4,834,735, which are all incorporated by reference herein.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1, which are all incorporated by reference herein.

Taped diapers may be manufactured and provided to consumers in a configuration wherein the front waist region and the back waist region are not fastened, pre-fastened, or connected to each other as packaged, prior to being applied to the wearer. For example, the taped diaper 100T may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The absorbent article 100 may also include various configurations of fastening elements to enable fastening of the front waist region 116 and the back waist region 118 together to form a closed waist circumference and leg openings once the absorbent article is positioned on a wearer. For example, as shown in FIGS. 1A and 1B, the absorbent article 100 may include first and second fastening members 162, 164, also referred to as tabs, connected with the first and second rear side panels 104, 106, respectively. The absorbent article may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302, which is incorporated by reference herein. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551, which is incorporated by reference herein.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846,815; 4,894,060; 4,946,527; 5,151,092; 5,221,274; 5,242,436; 6,251,097; 6,669,618; 6,432,098; U.S. Patent Publication Nos. 2007/0078427 A1 and 2007/0093769 A1; and U.S. patent application Ser. No. 16/685,230, which are all incorporated by reference herein.

As previously mentioned, the fastening members 162 and 164 may be constructed from various materials and may be constructed as a laminate structure. The fastening members 162 and 164 may also be adapted to releasably and/or refastenably engage or connect with another portion of the absorbent article 100. For example, as shown in FIG. 1A, the absorbent article 100 may include a connection zone 168, sometimes referred to as a landing zone, in the first waist region 116. As such, when the taped absorbent article 100 is placed on a wearer, the fastening members 162 and 164 may be pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the absorbent article. In some embodiments, the connection zone may be integrally formed as part of the backsheet 136 of the absorbent article 100 or may be formed as part of the first and second front panels 108, 110, such as described in U.S. Pat. Nos. 5,735,840 and 5,928,212, which are both incorporated by reference herein.

With continued reference to FIG. 1B, the absorbent article 100 may also include leg gasketing elements 156. It is to be appreciated that the leg gasketing elements 156 can be and are sometimes also referred to as leg cuffs, leg bands, side flaps, barrier cuffs, elastic cuffs or gasketing cuffs. The leg gasketing elements 156 may be elasticized and may be configured in various ways to help reduce the leakage of body exudates in the leg regions. Example leg gasketing elements 156 may include those described in U.S. Pat. Nos. 3,860,003; 4,909,803; 4,695,278; 4,795,454; 4,704,115; and U.S. Patent Publication No. 2009/0312730 A1, which are all incorporated by reference herein.

As shown in FIG. 1B, the absorbent article 100 may include longitudinally extending and laterally opposing leg gasketing elements 156 that are disposed on the interior surface 132 of the chassis 102 that faces inwardly toward the wearer and contacts the wearer. Each leg gasketing element 156 may have a first side edge 157 and a second side edge 159, wherein the first side edge 157 is positioned laterally inboard of the second side edge 159. The leg gasketing elements 156 may also overlap the absorbent assembly 140, wherein the first side edges 157 extend laterally inward of the respective side edges 152, 154 of the absorbent assembly 140. In some configurations, the leg gasketing elements 156 may not overlap the absorbent assembly 140. It is to be appreciated that the leg gasketing elements 156 may be formed in various ways, such as for example, by folding portions of the chassis 102 laterally inward, i.e., toward the longitudinal axis 124, to form both the respective leg gasketing elements and the side edges 128 and 130 of the chassis 102. In another example, the leg gasketing elements 156 may be formed by attaching an additional layer or layers to the chassis 102 at or adjacent to each of the respective side edges and of the chassis. Each of the leg gasketing elements 156 may be joined to the interior surface 132 of the chassis and/or the absorbent assembly 140 in leg gasketing element attachment zones in the front waist region 116 and in leg gasketing element attachment zones in the back waist region 118. The leg gasketing elements 156 may extend to the same longitudinal extent as the absorbent article 100 or alternatively the leg gasketing elements 156 may have a longitudinal extent that is less than the absorbent article 100. In some configurations, the leg gasketing elements may be configured to define inner cuffs, outer cuffs, or both inner and outer cuffs.

The absorbent article 100 may also include one or more waist panels 158, such as shown in FIG. 1B. The waist panel 158 may provide improved fit and containment and may define a portion or zone of the absorbent article 100 that may elastically expand and contract to dynamically fit a wearer's waist. The absorbent article 100 may also include more than one waist panels 158, for example, having a first panel 158a positioned in the first waist region 116 and second waistband 158b positioned in the second waist region 118, although other configurations may be constructed with a single waist panel 158. The waist panel 158 may be constructed in a number of different configurations including those described in U.S. Pat. Nos. 4,515,595 and 5,151,092, and U.S. patent application Ser. Nos. 16/864,267; 16/864,292; 62/855,001; 62/930,181; 62/930,198; and 62/930,808, which are all incorporated herein by reference.

It is to be appreciated that the waist panels 158 herein may be configured in various ways and may include one or more elastic materials, such as for example, elastic film and/or strands. For example, the waist panel 158 may be configured as a single layer of elastic film. In some configurations, the waist panel 158 may be configured as a laminate of two more substrates. For example, the waist panel 158 may be configured as an elastic film bonded in between two or more nonwoven substrates and/or may be bonded with one or more nonwoven substrates. For example, the waist panel 158 may be configured as a bi-laminate with an elastic film bonded with a single nonwoven substrate. In another example, the waist panel 158 may be configured as an elastic film bonded between two or more substrates, wherein the substrates may comprise nonwovens. It is also to be appreciated that nonwoven substrates of the waist panel 158 may be of the same or different material and/or basis weights and may be configured as an elastomeric nonwoven or a non-elastic nonwoven. In some configurations, one more nonwoven substrates of the waist panel 158 may be of the same or different material and/or basis weights as one more nonwoven substrates of the topsheet 138, backsheet 136, and/or leg gasketing elements 156.

It is to be appreciated that the waist panels 158 herein may be formed in various ways and may include various components bonded together in various ways and with differing or identical bond patterns. For example, the waist panels 158 herein may comprise a laminate of an elastic film bonded with at least one nonwoven in a stretched state. For example, as discussed in more detail below, FIGS. 18 and 19 show a cross sectional views of a waist panel 158 configured as a laminate 400 that includes a first substrate 402, a second substrate 410, and an elastic film 408 positioned between the first substrate 402 and the second substrate 410, wherein the first substrate 402 and/or second substrate 410 may be configured as a nonwoven as discussed above. In some configurations, the laminate may be bonded continuously or discontinuously. In some configurations, the laminate may be bonded with a plurality of individual bond sites that may or may not form a visually discernable pattern.

It is to be appreciated that components of the waist panel 158 may be bonded together in various ways, such as for example, by adhesive bonds, ultrasonic bonds, pressure bonds, thermal bonds or combinations thereof. It is to be appreciated that components of the waist panel 158 may be bonded together with adhesive applied in various ways, such as for example, as a spray nozzle and/or a slot coating device. In some configurations, components of the waist panel 158 may be continuously bonded with adhesive or bonded discontinuously with a patterned adhesive. In some configurations, the adhesive may be applied in accordance with the apparatuses and/or methods disclosed in U.S. Pat. Nos. 8,186,296; 9,265,672; 9,248,054; and 9,295,590 and U.S. Patent Publication No. 2014/0148773 A1, which are all incorporated by reference herein. In some configurations, components of the waist panel 158 may be mechanically (pressure) bonded with the application of pressure (and optionally heat) in various ways, such as for example, the mechanical bonding devices and methods disclosed in in U.S. Pat. Nos. 4,854,984; 6,248,195; 8,778,127; 9,005,392; 9,962,297; and 10,052,237, which are all incorporated by reference herein. In some configurations, components of the waist panel 158 may be mechanically (pressure) bonded with the use of ultrasonic bonding methods configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330.

In some configurations, the elastic film 408 may be bonded together with the first and/or second substrates 402, 410, and the first substrate 402 may be bonded directly to the second substrate 410 in areas of the waist panel 158. In some configurations, the first and second substrates 402, 410 may be bonded directly to each other through apertures in the elastic film 408, wherein such apertures may be formed during the bonding process. In some configurations, the elastic film 408 can be involved, or participate, in the bonding between the first and second substrates 402, 410, wherein "involved" can mean that the elastic film 408 can, to some extent, be in intimate contact with, and possibly partially merged with, one or both the first and second substrates 402, 410. The involvement may be due to actual melt bonding about the perimeter of a bond site or may be due to mechanical interaction, such as by entanglement of a fibrous elastic layer between fibrous nonwoven layers also about the perimeter of bond site. It is to be appreciated that the waist panel 158 may be formed with various types of bond configurations, such as disclosed, for example, in U.S. Pat. Nos. 6,572,595; 6,830,800; 7,087,287; and 7,803,244; and U.S. Patent Publication Nos. 2018/0042778 A1; 2018/0042787 A1; 2018/0042779 A1; and 2018/0042780 A1, which are all incorporated by reference herein.

In some configurations, the waist panel 158 may be formed as a zero strain stretch laminate that may be connected with the chassis 102 in a stretched state. In some configurations, the zero strain stretch laminate may include at least a layer of nonwoven material and an elastomeric element. The elastomeric element may be attached to the layer of nonwoven material while in a relaxed or substantially relaxed state, and the resulting laminate is made stretchable (or more stretchable over a further range) by subjecting the laminate to an activation process, which elongates the nonwoven layer permanently and elongates the elastomeric element temporarily. In some configurations, the nonwoven layer may be a separate component, in which case the elastomeric element is attached to the nonwoven layer to form the laminate, which is then connected with the chassis 102. In some configurations, the nonwoven layer may be integral with at least a portion of the chassis 102, in which case the elastomeric element may be attached to the nonwoven layer and the nonwoven/elastomeric element laminate is subsequently activated. In some configurations, the waist panel may be an extrusion bonded laminate. If one or more layers of the waist panel 158 are provided separately, the waist panel 158 may be activated either before or after attachment to the chassis 102. Examples of zero strain activation processes are disclosed in U.S. Pat. Nos. 5,167,897 and 5,156,793, which are incorporated by reference herein.

It is to be appreciated that the waist panel 158 may be located in various positions relative to the garment facing surfaces 132 and wearer facing surfaces 134 of various absorbent article components. In some configurations, the waist panel 158 may be positioned on the wearer facing surface 132 of the topsheet 138. In some configurations, the waist panel 158 may be positioned on the wearer facing surfaces 132 of the topsheet 138 and the leg gasketing elements 156. In some configurations, the waist panel 158 may be positioned on the wearer facing surfaces 132 of the topsheet 138 and laterally opposing end regions of the waistband 158 may be positioned between the leg gasketing elements 156 and the topsheet 138. In some configurations, the waist panel 158 may be positioned between the garment facing surface 132 of the topsheet 138 and the wearer facing surface 132 of the backsheet 136. And in some configurations, the waist panel 158 may be positioned on the garment facing surface 134 of the backsheet 136.

Figure 3:
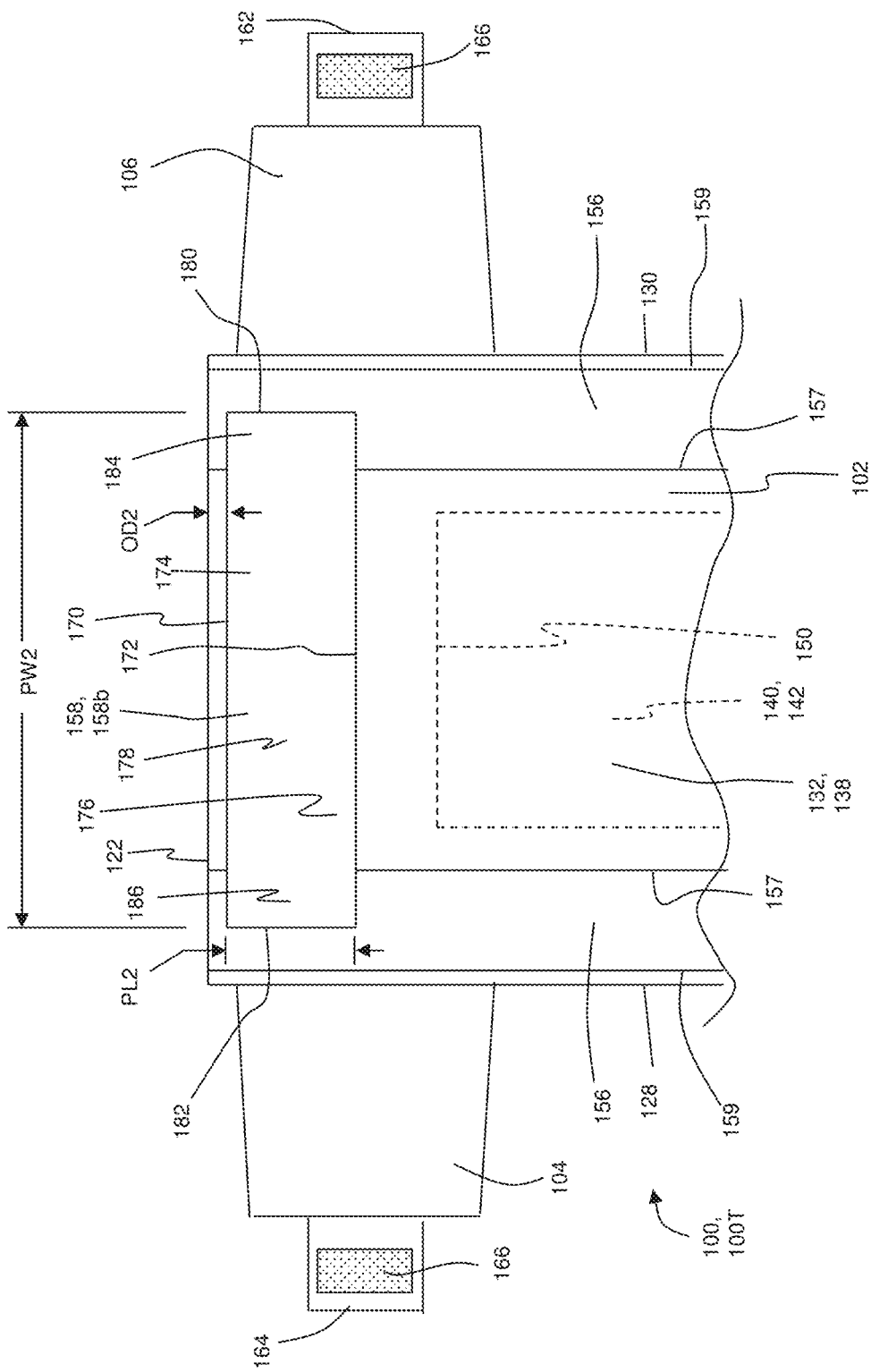
FIG. 3 is a detailed view of a second waist panel with the portion of the diaper that faces toward a wearer oriented towards the viewer.

As shown in FIGS. 2 and 3, the first and second waist panels 158a, 158b herein may each comprise a first lateral edge 170 and a second lateral edge 172, wherein the second lateral edge 172 is positioned longitudinally inward relative the first lateral edge 170. In addition, the first and second waist panels 158a, 158b may comprise a first longitudinal end region 174 adjacent the first lateral edge 170 and a second longitudinal end region 176 adjacent the second lateral edge 172, wherein the first and second longitudinal end regions 174, 176 are separated by a central region 178. The first and second lateral edges 170, 172 may be connected with and separated by a first longitudinal edge 180 and a second longitudinal edge 182. As such, the first and second waist panels 158a, 158b may also include a first lateral end region 184 adjacent the first longitudinal edge 180 and a second lateral end region 186 adjacent the second longitudinal edge 182, wherein the first and second lateral end regions 184, 186 are separated by the central region 178. In some configurations, the first lateral edge 170, second lateral edge 172, first longitudinal edge 180, and/or second longitudinal edge 182 may be defined by a fold line, wherein one or more layers of waist panel 158 may have been folded onto itself or another layer during assembly. In some configurations, the first lateral edge 170, second lateral edge 172, first longitudinal edge 180, and/or second longitudinal edge 182 may be defined by unfolded edge or a cut line, wherein one or more layers of waist panel 158 may have been cut or trimmed during assembly.

It is to be appreciated that the waist panels 158 herein may be configured with various shapes and/or sizes. For example, as shown in FIGS. 2 and 3, the first waist panel 158a may comprise a first width PW1 extending between first and second longitudinal edges 180, 182, and the second waist panel 158b may comprise a second width PW2 extending between first and second longitudinal edges 180, 182. It is to be appreciated that the first width PW1 and the second width PW2 may be equal or different. In some configurations, the first width PW1 and/or the second width PW2 may be from about 80 mm to about 250 mm, specifically reciting all 1 mm increments within the above-recited ranges and all ranges formed therein or thereby. The first waist panel 158a may comprise a first length PL1 extending between first and second lateral edges 170, 172, and the second waist panel 158b may comprise a second length PL2 extending between first and second lateral edges 170, 172. It is to be appreciated that the first length PL1 and the second length PL2 may be equal or different. In some configurations, the first length PL1 and/or the second length PL2 may be from about 5 mm to about 80 mm, specifically reciting all 1 mm increments within the above-recited ranges and all ranges formed therein or thereby.

It is to be appreciated that the waist panels 158 may be located in various lateral and longitudinal positions relative to various absorbent article components. In some configurations, the waist panel 158 may be positioned such that the first and second longitudinal edges 180, 182 of the waist panel 158 are located laterally inboard of the leg gasketing elements 156. In some configurations, the waist panel 158 may be positioned such that the first and second longitudinal edges 180, 182 and the first and second longitudinal end regions 174, 176 of the waist panel 158 overlap the leg gasketing elements 156. In some configurations, the first waist panel 158a may be positioned longitudinally inboard from the first waist edge 120 of the absorbent article 100 and/or toward or overlapping the first lateral edge 148 of the absorbent core 142; and the second waist panel 158b may be positioned longitudinally inboard from the second waist edge 122 of the absorbent article 100 and/or toward or overlapping the second lateral edge 150 of the absorbent core 142. In some configurations, the first lateral edge 170 of the first waist panel 158a may be positioned longitudinally inboard from the first waist edge 120 by an offset distance OD1 that is greater than zero. In some configurations, the first lateral edge 170 of the second waist panel 158b may be positioned longitudinally inboard from the second waist edge 122 by an offset distance OD2 that is greater than zero. In some configurations, the offset distance OD1 and/or the offset distance OD2 may be at least 5 mm. In some configurations, the first lateral edge 170 of the first waist panel 158a may be coterminous with the first waist edge 120 such that the offset distance OD1 is zero. In some configurations, the first lateral edge 170 of the second waist panel 158b may be coterminous with the second waist edge 122 such that the offset distance OD2 is zero.

It is to be appreciated that the first waist panel 158a and/or the second waist panel 158b may be bonded with the chassis 102 and/or leg gasketing elements 156 in various ways, such as for example, by adhesive bonds, ultrasonic bonds, pressure bonds, thermal bonds or combinations thereof. It is to be appreciated that the first waist panel 158a and/or the second waist panel 158b may be bonded with the chassis 102 and/or leg gasketing elements 156 with adhesive applied in various ways, such as for example, as a spray nozzle and/or a slot coating device. In some configurations, the first waist panel 158a and/or the second waist panel 158b may be continuously bonded with the chassis 102 and/or leg gasketing elements 156 with adhesive or bonded discontinuously with a patterned adhesive. In some configurations, the adhesive may be applied in accordance with the apparatuses and/or methods disclosed in U.S. Pat. Nos. 8,186,296; 9,265,672; 9,248,054; and 9,295,590 and U.S. Patent Publication No. 2014/0148773 A1, which are all incorporated by reference herein. In some configurations, the first waist panel 158a and/or the second waist panel 158b may be mechanically (pressure) bonded with the chassis 102 and/or leg gasketing elements 156 with the application of pressure (and optionally heat) in various ways, such as for example, the mechanical bonding devices and methods disclosed in in U.S. Pat. Nos. 4,854,984; 6,248,195; 8,778,127; 9,005,392; 9,962,297; and 10,052,237, which are all incorporated by reference herein. In some configurations, the first waist panel 158a and/or the second waist panel 158b may be mechanically (pressure) bonded with the chassis 102 and/or leg gasketing elements 156 with the use of ultrasonic bonding methods configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330.

Figure 2A:
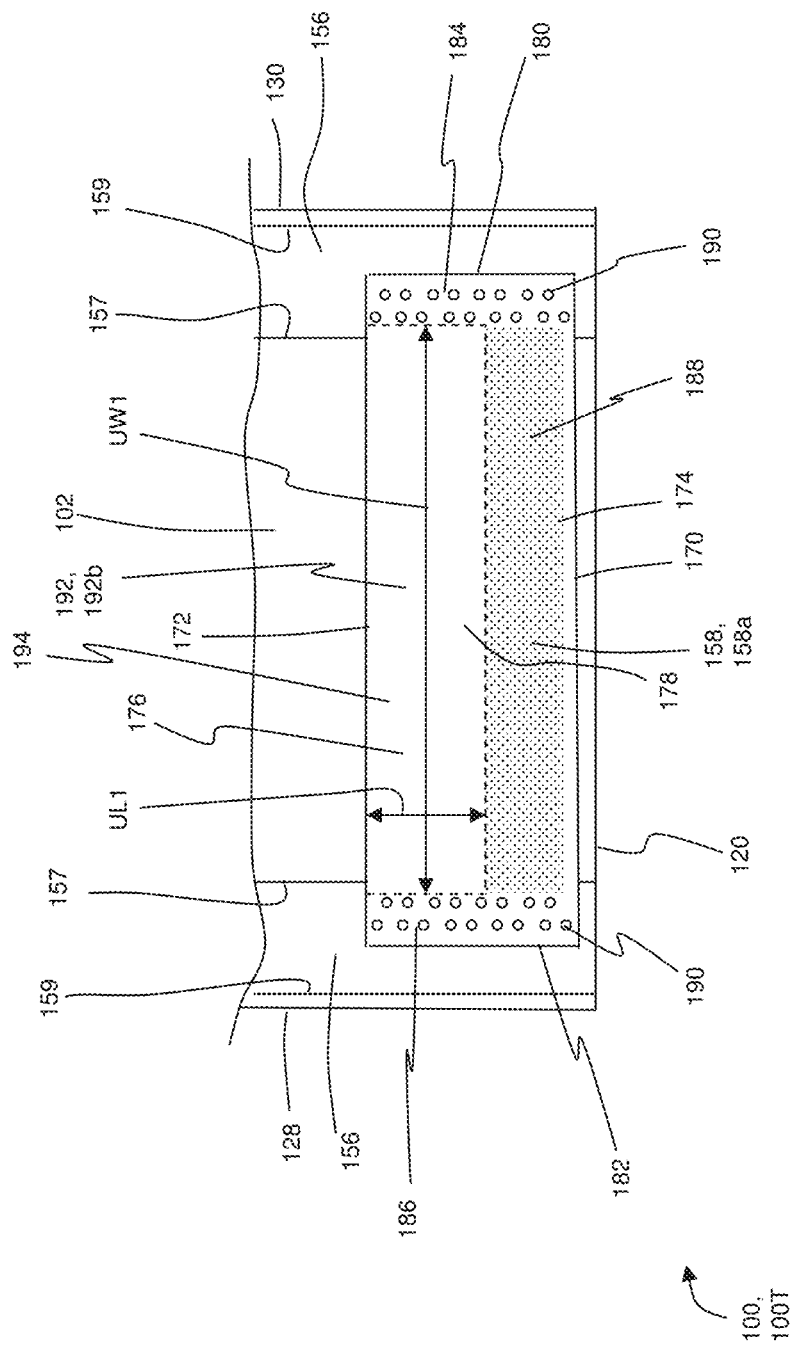
FIG. 2A is a detailed view of the first waist panel from FIG. 2 illustrating bonding configurations.
Figure 3A:
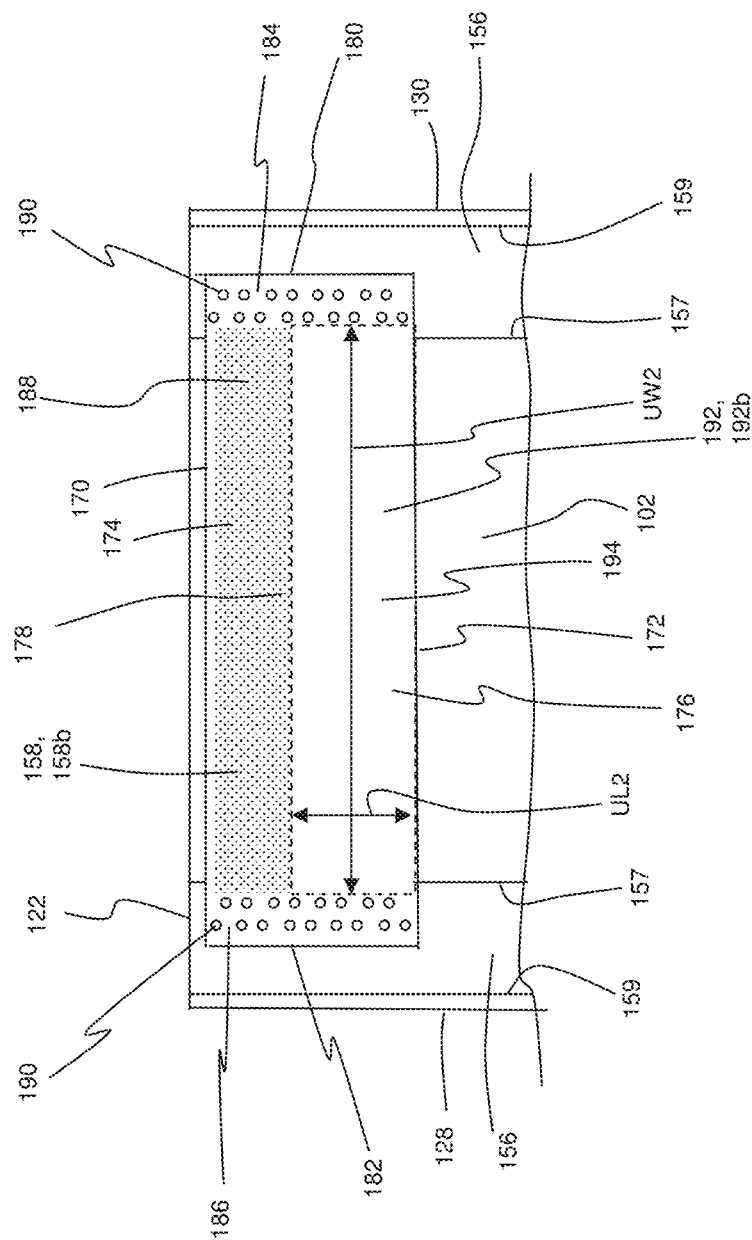
FIG. 3A is a detailed view of a second waist panel from FIG. 3 illustrating bonding configurations.

As previously mentioned, it is to be appreciated that the waist panels 158 herein may be bonded with the chassis 102 and/or leg gasketing elements 156 with combinations of adhesive bonds and pressure bonds. For example, as shown in FIG. 2A, the first longitudinal end region 174 of the first waist panel 158a may be bonded with the chassis 102 and/or leg gasketing elements 156 with adhesive bonds 188, which are generically illustrated by a shaded region. In addition, the first and second lateral end regions 184, 186 of the first waist panel 158a may be bonded with the chassis 102 and/or leg gasketing elements 156 with pressure bonds 190. In some configurations, the first and second lateral end regions 184, 186 of the first waist panel 158a may be bonded with inner cuffs and/or outer cuffs of leg gasketing elements 156. As shown in FIG. 3A, the first longitudinal end region 174 of the second waist panel 158b may be bonded with the chassis 102 and/or leg gasketing elements 156 with adhesive bonds 188, which are generically represented by a shaded region. In addition, the first and second lateral end regions 184, 186 of the second waist panel 158b may be bonded with the chassis 102 and/or leg gasketing elements 156 with pressure bonds 190. In some configurations, the first and second lateral end regions 184, 186 of the second waist panel 158b may be bonded with inner cuffs and/or outer cuffs of leg gasketing elements 156. In some configurations, the pressure bonds 190 may be a discontinuous pattern of discrete bond sites. It is to be appreciated that the discrete bond sites may define various sizes and shapes and may be separated from each other by various distances. For example, in some configurations, the discrete bond sites may be separated from each other by at least 0.2 mm. It is also to be appreciated that the discrete bond sites may cover various different sized areas of the waist panel. For example, in some configurations, the plurality of discrete bond sites may comprise from about 5% to about 50% of an area of the waist panel. In some configurations, the first and second lateral end regions 184, 186 extending along the first and second longitudinal edges 180, 182 may be bonded with the chassis 102 and/or leg gasketing elements 156 with a continuous bond that defines a sealed edge.

In some configurations, one or more regions of the waist panel 158 (referred to herein as bond regions) may be bonded with the chassis 102 and/or leg gasketing elements 156, and one or more regions of the waist panel 158 (referred to as unbonded regions 192) may not be bonded (unattached) with the chassis 102 and/or leg gasketing elements 156, thereby forming a pocket 194 between the waist panel 158 and the chassis 102. For example, as shown in FIG. 2A, the first waist panel 158a may comprise bonded regions wherein the first longitudinal end region 174, the first lateral end region 184, and the second lateral end region 186 of the first waist panel 158a are bonded with chassis 102 and/or leg gasketing elements 156; and the first waist panel 158a may comprise at least one unbonded region 192a (generically illustrate by a rectangle with a dashed border) wherein a portion of the second longitudinal end region 176 and at least a portion the second lateral edge 172 may be unattached to the chassis 102 and/or leg gasketing elements 156. With continued reference to FIG. 3A, the second waist panel 158b may comprise bonded regions wherein the first longitudinal end region 174, the first lateral end region 184, and the second lateral end region 186 of the second waist panel 158b are bonded with chassis 102 and/or leg gasketing elements 156; and the second waist panel 158b may comprise at least one unbonded region 192b (generically illustrate by a rectangle with a dashed border) wherein a portion of the second longitudinal end region 176 and at least a portion the second lateral edge 172 may be unattached to the chassis 102 and/or leg gasketing elements 156.

It is to be appreciated that the waist panels 158 herein may be configured with one or more unbonded regions with various shapes and/or sizes. For example, as shown in FIGS. 2A and 3A, the first waist panel 158a may comprise a first unbonded region 192a and/or the second waist panel 158b may comprise a second unbonded region 192b. As such, the first unbonded region 192a may comprise a laterally extending first width UW1 and a longitudinally extending first length UL1, and the second unbonded region 192b may comprise a laterally extending second width UW2 and a longitudinally extending second length UL2. It is to be appreciated that the first width UW1 and the second width UW2 may be equal or different. In some configurations, the first width UW1 and/or the second width UW2 may be from about 40 mm to about 200 mm, specifically reciting all 1 mm increments within the above-recited ranges and all ranges formed therein or thereby. It is also to be appreciated that the first length UL1 and the second length UL2 may be equal or different. In some configurations, the first length UL1 and/or the second length UL2 may be from about 10 mm to about 50 mm, specifically reciting all 1 mm increments within the above-recited ranges and all ranges formed therein or thereby. In some configurations, the first unbonded region 192a may comprise a first area A1 and/or the second unbonded region 192b may comprise a second area A2, wherein the first area A1 and the second area may be equal or different. In some configurations, the first area A1 and/or the second area A2 may be from about 400 $mm^2$ to about 10000 $mm^2$, specifically reciting all 1 $mm^2$ increments within the above-recited ranges and all ranges formed therein or thereby.

It is also to be appreciated that in some configurations, one or more regions of the waist panel 158 may be bonded with the chassis 102 and/or leg gasketing elements 156 relatively completely in lateral and/or longitudinal directions such that a pocket 194 is not formed between the waist panel 158 and the chassis 102.

As discussed above, the waist panels 158 herein may be elastic and may comprise at least one direction of stretch. In some configurations, the direction of stretch may be laterally oriented between the first longitudinal edge 180 and the second longitudinal edge 182. In some configurations, the first waist panel 158a and/or the second waist panel 158b may be configured to extend at least about 10 mm with an applied force greater than 0 to about 3N. It is also to be appreciated that the first waist panel 158a may comprise stretch characteristics that are the same or different from stretch characteristics of the second waist panel 158b. Such stretch characteristics may comprise a percent contraction or a percent elongation. In some configurations, the stretch characteristics of the first waist panel 158a may be the same or may vary between the first lateral edge 170 and the second lateral edge 172 and/or the between the first longitudinal edge 180 and the second longitudinal edge 182. And in some configurations, the stretch characteristics of the second waist panel 158b may be the same or may vary between the first lateral edge 170 and the second lateral edge 172 and/or the between the first longitudinal edge 180 and the second longitudinal edge 182.

It is to be appreciated that desired stretch characteristics of the waist panels 158 herein may be imparted to the waist panels 158 in various ways, such as before, during, or after the waist panel 158 is combined with chassis 102 and/or the leg gasketing elements 156. For example, structural features may be imparted to one or more individual components of the waist panel 158 before, during, and/or after assembly of the waist panel 158 to provide desired stretch characteristics of the waist panel 158. In some configurations, structural features may be imparted to the waist panel 158, the chassis 102, and/or the combined waist panel 158 and chassis 102 to provide desired stretch characteristics of the waist panel 158. In some configurations, the same structural features may be imparted to the first waist panel 158a and/or the second waist panel 158b to help ensure the first and second waist panels 158a, 158b comprise similar stretch characteristics. In some configurations, different structural features may be imparted to the first waist panel 158a and/or the second waist panel 158b to help ensure the first and second waist panels 158a, 158b comprise different stretch characteristics.

Figure 2B:
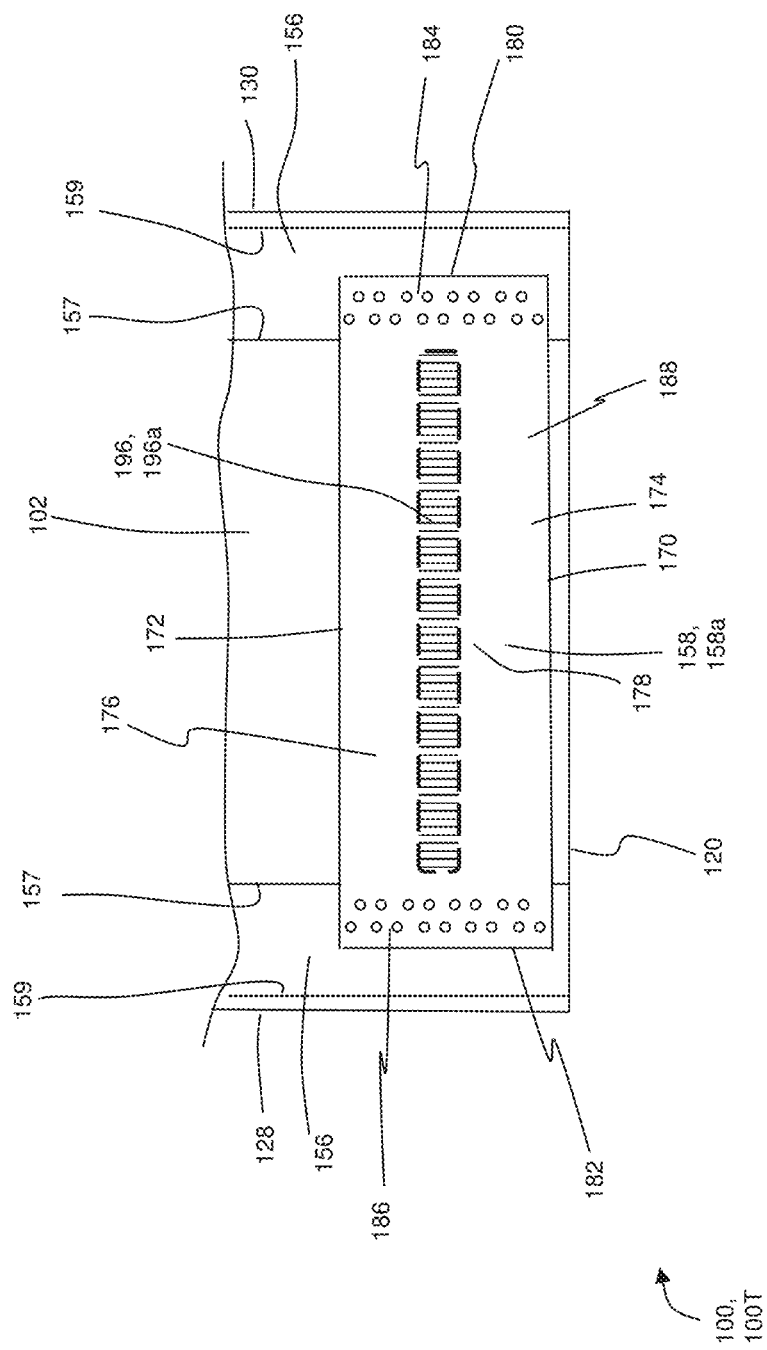
FIG. 2B is a detailed view of the first waist panel from FIG. 2 illustrating structural features.
Figure 3B:
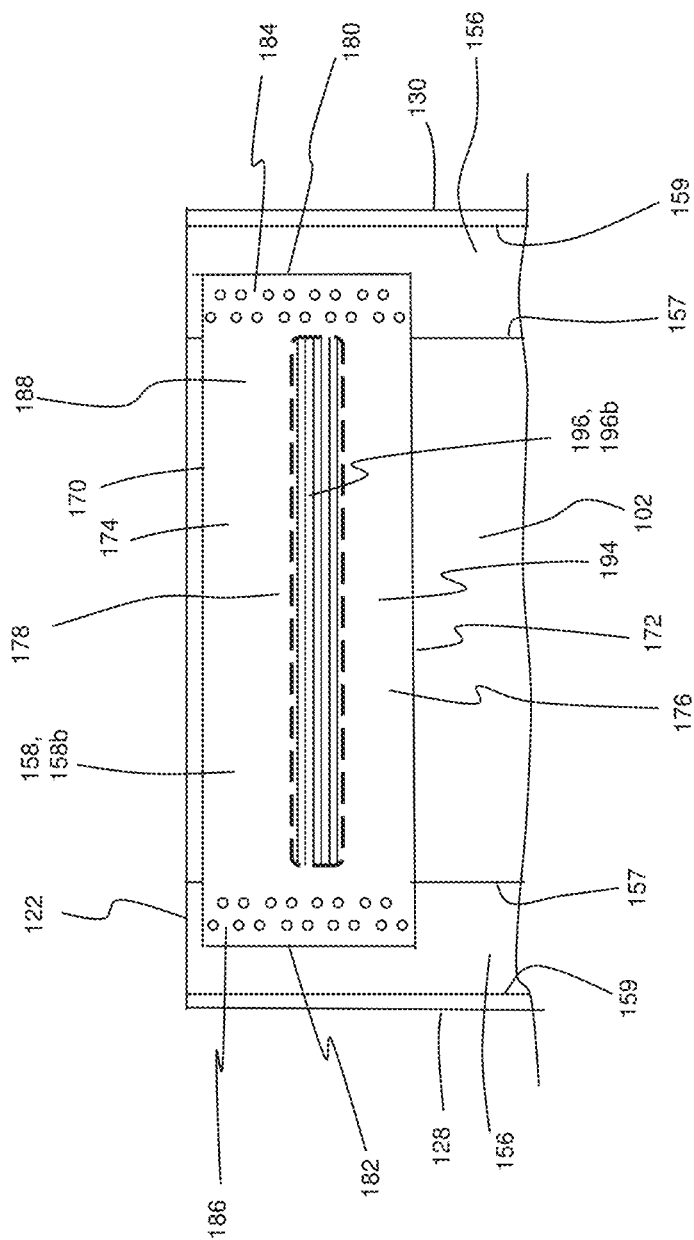
FIG. 3B is a detailed view of a second waist panel from FIG. 3 illustrating structural features.

FIGS. 2B and 3B show an example absorbent article configuration wherein first waist panel 158a comprises a first structural feature 196a and the second waist panel 158b comprises a second structure feature 196b. The first and second structural features 196a, 196b are generically illustrated as rectangles with patterned fill. Thus, it is to be appreciated that the first structural feature 196a of the first waist panel 158a may be different from the second structural feature 196b of the second waist panel 158b, wherein the first structural feature 196a and the second structural feature 196b may provide different stretch characteristics between the first waist panel 158a and the second waist panel 158b. In another example, the first waist panel 158a may comprise a first structural feature 196a that is not included in the second waist panel 158b, and/or the second waist panel 158b may comprise a second structural feature 196b that is not included in the first waist panel 158a.

It is to be appreciated that the first structural features 196a and/or the second structural features 196b may comprise various forms, such as for example, embossing, apertures, slits, melted material, compressed material, plastic deformation, folds, adhesive bonds, and/or pressure bonds and may be formed in various ways, such as for example, by the application ultrasonic energy, laser energy, pressure, heat, adhesive, folds, and/or cuts. In some configurations, the first structural features 196a and/or the second structural features 196b may be formed by cutting and removing discrete pieces from the first waist panel 158a and/or the second waist panel 158b. In some configurations, the first structural feature 196a and/or the second structural feature 196b comprise an amount by which the first waist panel 158a and/or the second waist panel 158b is stretched when bonded with the chassis 102 and/or leg gasketing elements 156. For example, the first waist panel 158a and the second waist panel 158b may be bonded with the chassis 102 in a stretched state, wherein the first waist panel 158a is stretched less than or greater that the second waist panel 158b when bonded with the chassis 102. In some configurations, a stiffening element may be used to provide different stretch characteristics between the first waist panel 158a and the second waist panel 158b. For example, the stiffening element may be disposed on the first waist panel 158a and/or the second waist panel 158b. In some configurations, the stiffening element may comprise a substrate, such as for example, a discrete patch of nonwoven.

In some configurations, the first waist panel 158a and the second waist panel 158b may comprise the same structural features 196 in different areas and/or regions so as to impart different stretch characteristics. For example, the first waist panel 158a may comprise a first structural feature 196a adjacent the first lateral edge 170 and the second waist panel 158b may comprise the same first structural feature 196a adjacent the first lateral edge 170, wherein the first structural feature 196a may extend for different longitudinal lengths and/or lateral widths on the first waist panel 158a and the second waist panel 158b.

Figure 3C:
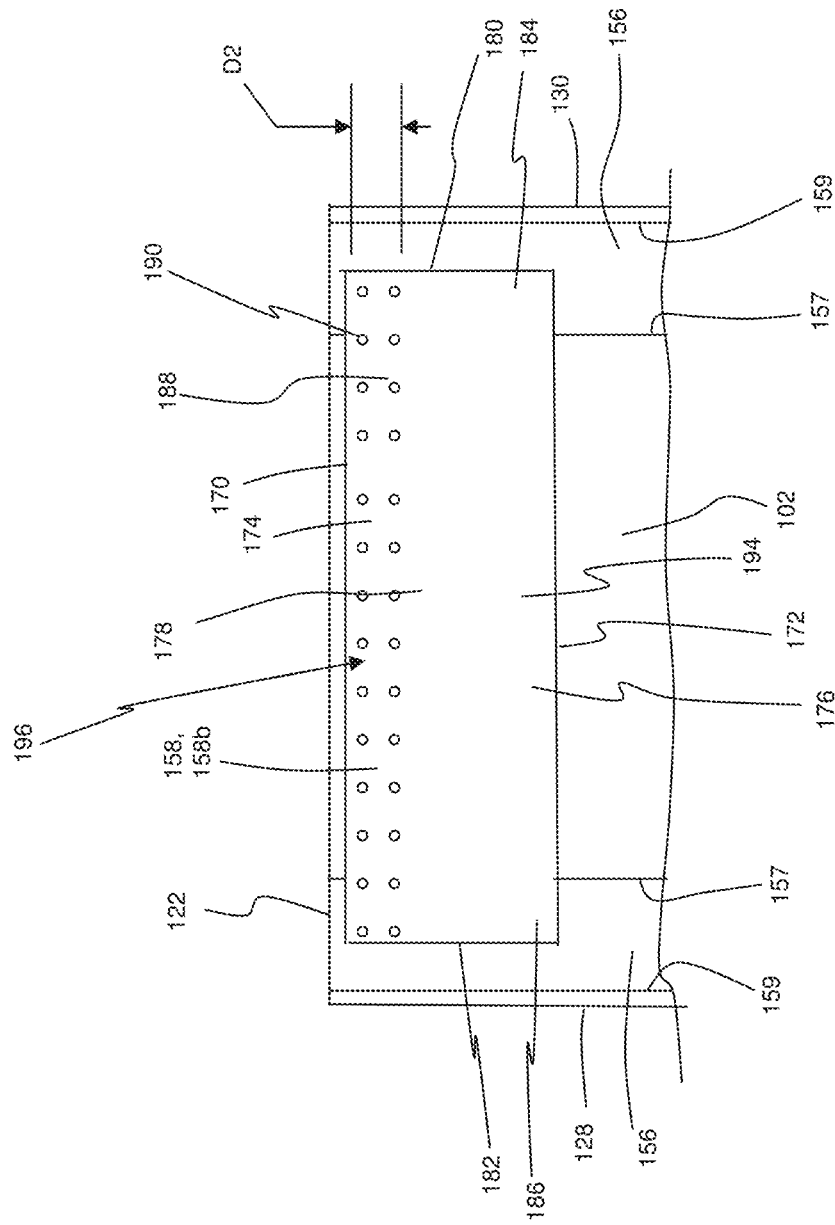
FIG. 3C is a detailed view of a second waist panel from FIG. 3 illustrating a structural configuration with pressure bonds.
Figure 4:
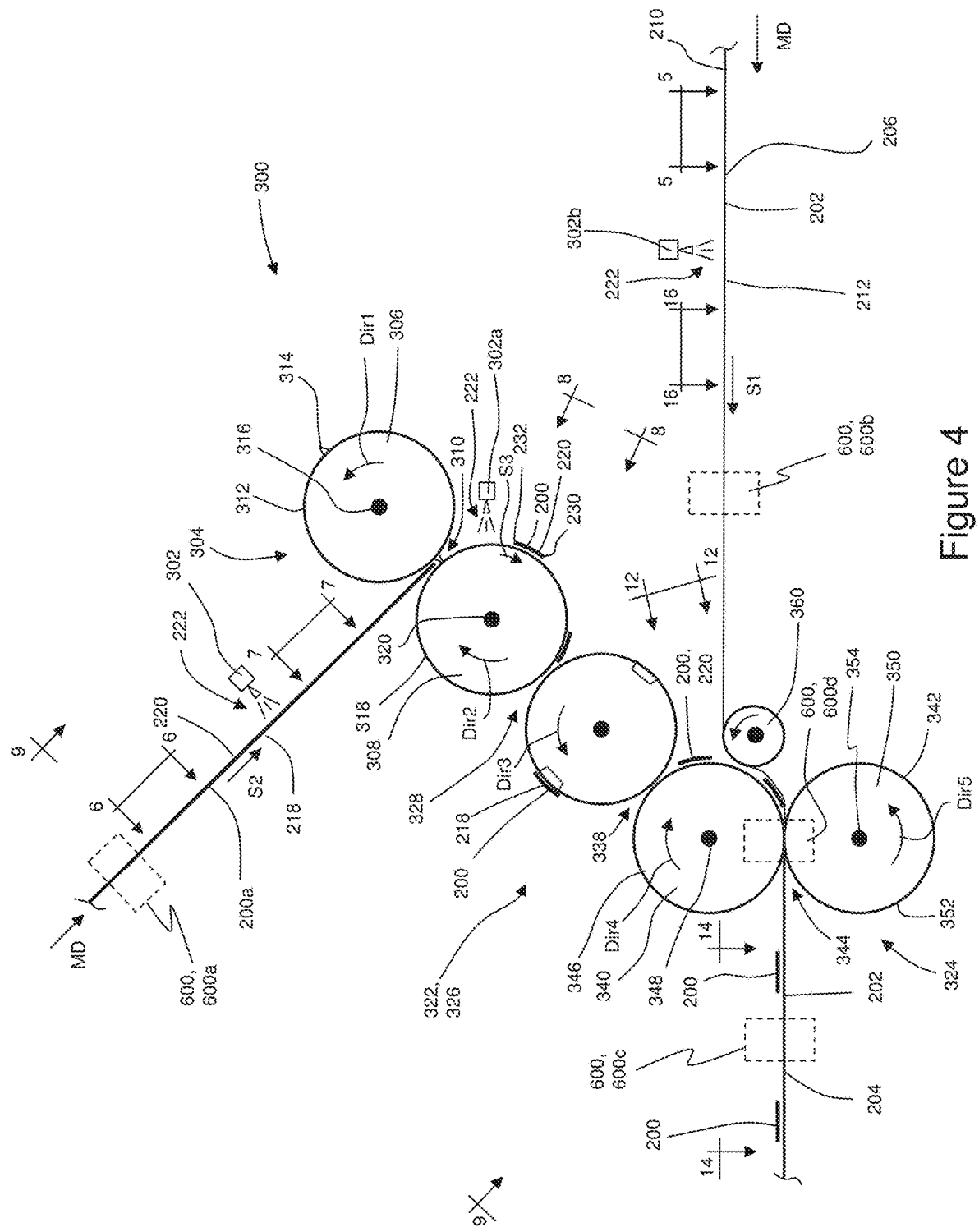
FIG. 4 is a schematic side view of an apparatus for bonding elastic parts to an advancing carrier web.

FIGS. 2C and 3C shows an example illustration wherein the first waist panel 158a comprises comprising a structural feature 196 in the form of pressure bonds 190, and the second waist panel 158b comprises the same structural feature 196 in the form of pressure bonds 190. A first region of pressure bonds 190 may extend longitudinally inboard from the first lateral edge 170 of the first waist panel 158a by a first distance D1 and a second region of pressure bonds 190 may extend longitudinally inboard from the first lateral edge 170 of the second waist panel 158b by a second distance D2. In some configurations, the first distance D1 may greater than or less than the second distance D2, and as such, the pressure bonds 190 may impart different stretch characteristics to the first and second waist panels 158a, 158b. It is to be appreciated that the first distance D1 and the second distance D2 may extend for various lengths. In some configurations, the first distance D1 and/or the second distance D2 may extend for the entire lengths PL1, PL2 of the first and/or second waist panels 158a, 158b, respectively. In some configurations, the first distance D1 may extend longitudinally inboard of the first lateral edge 170 of the first waist panel 158a for a distance of 10 mm or less, and/or the second distance D2 may extend longitudinally inboard of the first lateral edge 170 of the second waist panel 158b for a distance of 10 mm or less. It is to be appreciated that absorbent articles 100 may be assembled with various components, including waist panels 158, described herein in various ways. Thus, in the context of the previous discussion, various apparatuses and methods may be adapted to assemble absorbent articles 100 with first waist panels 158a and second waist panels 158b with structural features that impart different stretch characteristics to the first and second waist panels 158a, 158b. For example, FIG. 4 shows a schematic representation of a converting process including an apparatus or system 300 that bonds discrete elastic parts 200 under tension with an advancing carrier substrate 202 to form a laminate 204 during the assembly of an absorbent article 100. Various aspects of the apparatuses 300 and associated assemblies shown in FIG. 4 are disclosed in U.S. patent application Ser. Nos. 16/864,267; 16/864,292; 62/855,001; 62/930,181; 62/930,198; and 62/930,808, which are all incorporated herein by reference.

Figure 5:
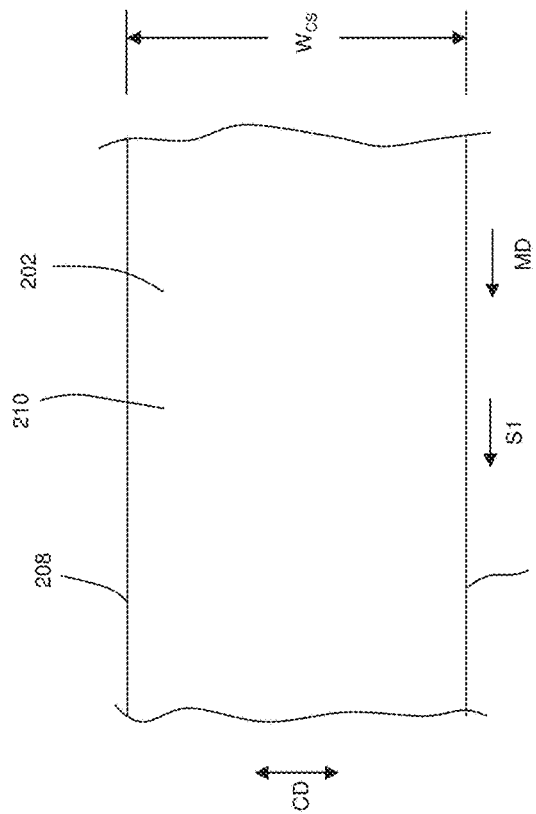
FIG. 5 is a view of a carrier substrate taken along section 5-5 in FIG. 4.

As shown in FIGS. 4 and 5, the carrier substrate 202 may advance in a machine direction MD at a first speed S1. The carrier substrate comprises a first longitudinal edge 206 and a second longitudinal edge 208 separated from the first longitudinal edge 206 in a cross direction CD to define a width $W_{CS}$. The carrier substrate 202 also includes a first surface 210 and an opposing second surface 212. As discussed in more detail below, discrete elastic parts 200 are bonded with the first surface 210 of the carrier substrate 202.

In the context of components of absorbent articles 100 discussed above and assembly processes thereof, the elastic parts 200 may be configured as waist panels 158. In some configurations, each discrete elastic part 200 may be configured as a first waist panel 158a, a second waist panel 158b, or may be a part that is subsequently cut along with the carrier substrate 202 to be formed into a first waist panel 158a and a second waist panel 158b. The carrier substrate 202 may be configured as a continuous topsheet 138, backsheet 136, or continuous laminate of a combined topsheet 138 and backsheet 136 that may also be part of a continuous length of chassis 102. The laminate 204 may be configured as a continuous length of absorbent articles 100. In some configurations, the first surface 210 of the carrier substrate 202 may correspond with the wearer facing surface 132 or the garment facing surface 134 of the topsheet 138 or backsheet 136. In some configurations, the elastic part 200 may be bonded between a topsheet 138 and a backsheet 136. For example, the elastic part 200 may be bonded with the wearer facing surface 132 of the backsheet 136, which is subsequently bonded with a topsheet 138. In another example, the elastic part 200 may be bonded with the garment facing surface 134 of the topsheet 138, which is subsequently bonded with a backsheet 136. In yet another example, the elastic part 200 may be bonded with the garment facing surface 134 of the backsheet 136, wherein the wearer facing surface 132 of the backsheet 136 may have been previously bonded with a topsheet 138 or may be subsequently bonded with a topsheet 138. In another example, the elastic part 200 may be bonded with the wearer facing surface 132 of the topsheet 136, wherein the garment facing surface 134 of the topsheet 138 may have been previously bonded with a backsheet 136 or may be subsequently bonded with a backsheet 136.

As shown in FIG. 5A, the carrier substrate 202 may also include leg gasketing elements 156 positioned on the first surface 210 adjacent the first longitudinal edge 206 and the second longitudinal edge 208. As such, portions of the discrete elastic parts 200 may also be bonded with the leg gasketing elements 156. In some configurations, the discrete elastic parts 200 may be bonded with the carrier substrate 202 and leg gasketing elements 156 may subsequently be bonded with the carrier substrate 202. The leg gasketing elements 156 may be positioned relative the elastic part 200 such that the leg gasketing elements 156 may or may not partially cover or overlap opposing end portions of the elastic part 200. In some configurations, the leg gasketing elements 156 may be sandwiched between the elastic parts 200 and the carrier substrate 202. And in some configurations, the elastic parts 200 may be sandwiched between the leg gasketing elements 156 and the carrier substrate 202.

Referring now to FIGS. 4 and 6, a continuous elastic substrate 200a is advanced at a second speed S2 in a machine direction MD, wherein the second speed S2 is less than the first speed S1. The continuous elastic substrate 200a comprises a first longitudinal edge 214 and a second longitudinal edge 216 separated from the first longitudinal edge 214 in the cross direction CD to define a width $W_{ES}$. The continuous elastic substrate 200a also includes a first surface 218 and an opposing second surface 220. The continuous elastic substrate 200a is stretchable in at least one direction and is oriented such that the continuous elastic substrate 200a is stretchable in the cross direction CD. As such, the width $W_{ES}$ of the continuous elastic substrate may be an unstretched width. In some configurations, the width $W_{ES}$ of the continuous elastic substrate 200a may be a partially stretched width.

With continued reference to FIGS. 4, 6, and 7, the system 300 may include an adhesive applicator device 302 that deposits adhesive 222 onto the second surface 220 of the continuous elastic substrate 200a. It is to be appreciated that the adhesive applicator device 302 may be configured in various way, such as for example, as a spray nozzle and/or a slot coating device. In some configurations, the adhesive applicator device 302 may be configured in accordance with the apparatuses and/or methods disclosed in U.S. Pat. Nos. 8,186,296; 9,265,672; 9,248,054; and 9,295,590 and U.S. Patent Publication No. 2014/0148773 A1, which are all incorporated by reference herein.

It is to be appreciated that the adhesive 222 may be applied to the continuous elastic substrate 200a to define regions of adhesive 222 on the second surface 220 having various shapes and sizes relative to the continuous elastic substrate 200a. For example, as shown in FIG. 7, the adhesive 222 may be applied to the second surface 220 of the continuous elastic substrate 200a to define a region 224 of adhesive 222 extending continuously in the machine direction MD and the cross direction CD. The adhesive 222 may extend in the cross direction CD define a width $W_{ADH}$. In some configurations, the width $W_{ADH}$ of adhesive 222 may be less than the width $W_{ES}$ of the continuous elastic substrate 200a, and in some configurations, the width $W_{ADH}$ may be equal to the width $W_{ES}$ of the continuous elastic substrate 200a.

Figure 8:
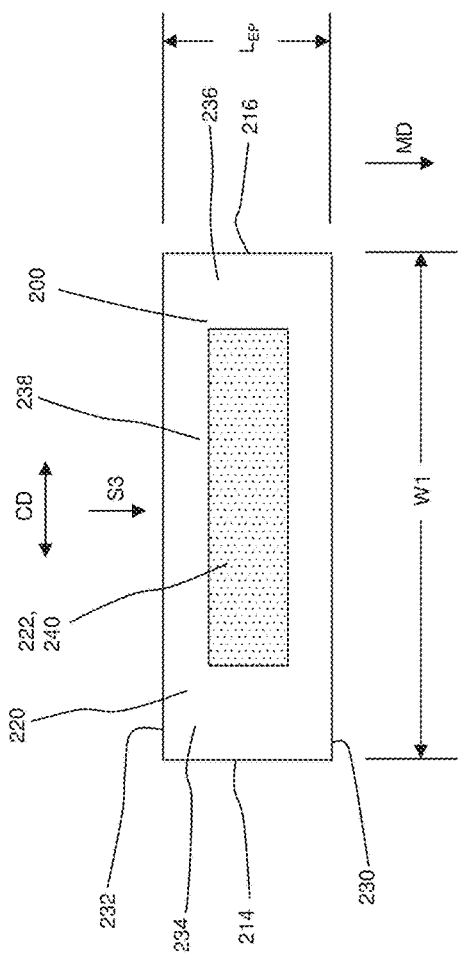
FIG. 8 is a view of a discrete elastic part laid out flat with a zone of adhesive thereon taken along section 8-8 in FIG. 4.

As shown in FIGS. 4, 7, and 8, the continuous elastic substrate 200a may advance in the machine direction MD from the adhesive applicator device 302 to a cutting device 304 that cuts and separates discrete elastic parts 200 from the continuous elastic substrate 200a. As such, the discrete elastic parts 200 each include a leading edge 230 and a trailing edge 232 and defines a length $L_{EP}$ in the machine direction MD extending from the leading edge 230 to the trailing edge 232. The elastic part 200 also includes first and second longitudinal edges 214, 216 that correspond with the longitudinal edges 214, 216 of the continuous elastic substrate 200a extending between the leading and trailing edges 230, 232. In addition, the elastic part 200 includes first and second surfaces 218, 220 that correspond with the first and second surfaces 218, 220 of the continuous elastic substrate 200a.

As shown in FIG. 8, the discrete elastic part 200 also includes a first end region 234 adjacent the first longitudinal edge 214 and a second end region 236 adjacent the second longitudinal edge 216, wherein the second end region 236 is separated from the first end region 234 in the cross direction CD by a central region 238. As discussed above, adhesive 222 may be applied to the second surface 220 of the continuous elastic substrate 200a. As such, the discrete elastic part 200 may include a zone 240 of adhesive 222 on the second surface 220. It is to be appreciated that the zone 240 of adhesive 222 may define various sizes and shapes relative to the elastic part 200. For example, as shown in FIG. 8, the zone 240 of adhesive may extend in the cross direction CD for less than the entire width W1 of the discrete elastic part 200. In some configurations, the zone 240 of adhesive 222 may be positioned only on the central region 238 of the discrete elastic part 200 such that the first end region 234 and the second end region 236 of the second surface 220 of the discrete elastic part 200 may not include any adhesive 222.

Figure 9:
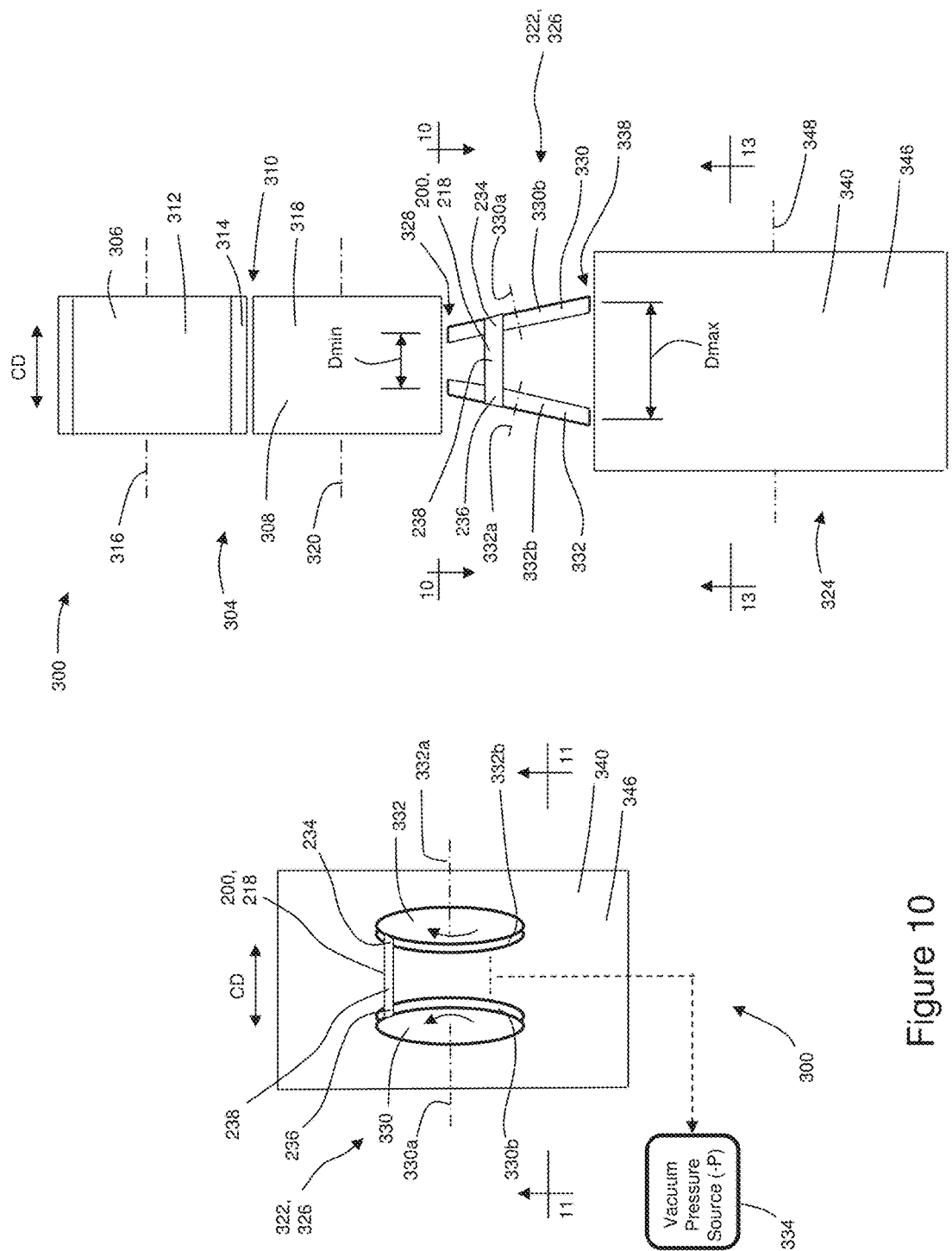
FIG. 9 is a view of a cutting device, transfer device, and bonding device taken along section 9-9 in FIG. 4.

As shown in FIGS. 4 and 9, the cutting device 304 may include a knife roll 306 positioned adjacent an anvil roll 308 to define a nip 310 therebetween. The knife roll 306 may include an outer circumferential surface 312 and one or more blades 314 adapted to rotate about an axis 316 in a first direction Dir1. The anvil roll 308 may include an outer circumferential surface 318 adapted to rotate about an axis 320 in a second direction Dir2 opposite the first direction Dir1 such that the outer circumferential surface 318 advances at a third speed S3, wherein the third speed S3 is greater than the second speed S2. With continued reference to FIG. 4, as the continuous elastic substrate 200a advances through the nip 310 between the knife roll 306 and the anvil roll 310, the blade 314 operates to cut the discrete elastic part 200 from the continuous elastic substrate 200a. Because the outer circumferential surface 318 of the anvil roll 308 advances at the third speed S3, the cut discrete elastic part 200 may then accelerate from the second speed S2 to the third speed S3 on the outer circumferential surface 318 of the anvil roll 308. It is also to be appreciated that one or more components of the cutting device 304 may be configured to operate at constant and/or variable speeds. For example, the knife roll 306 and/or the anvil roll 308 may be connected with various types of motors, such as servo motors for example, that may rotate the knife roll 306 and/or the anvil roll 308 at constant and/or variable angular velocities.

Figure 14:
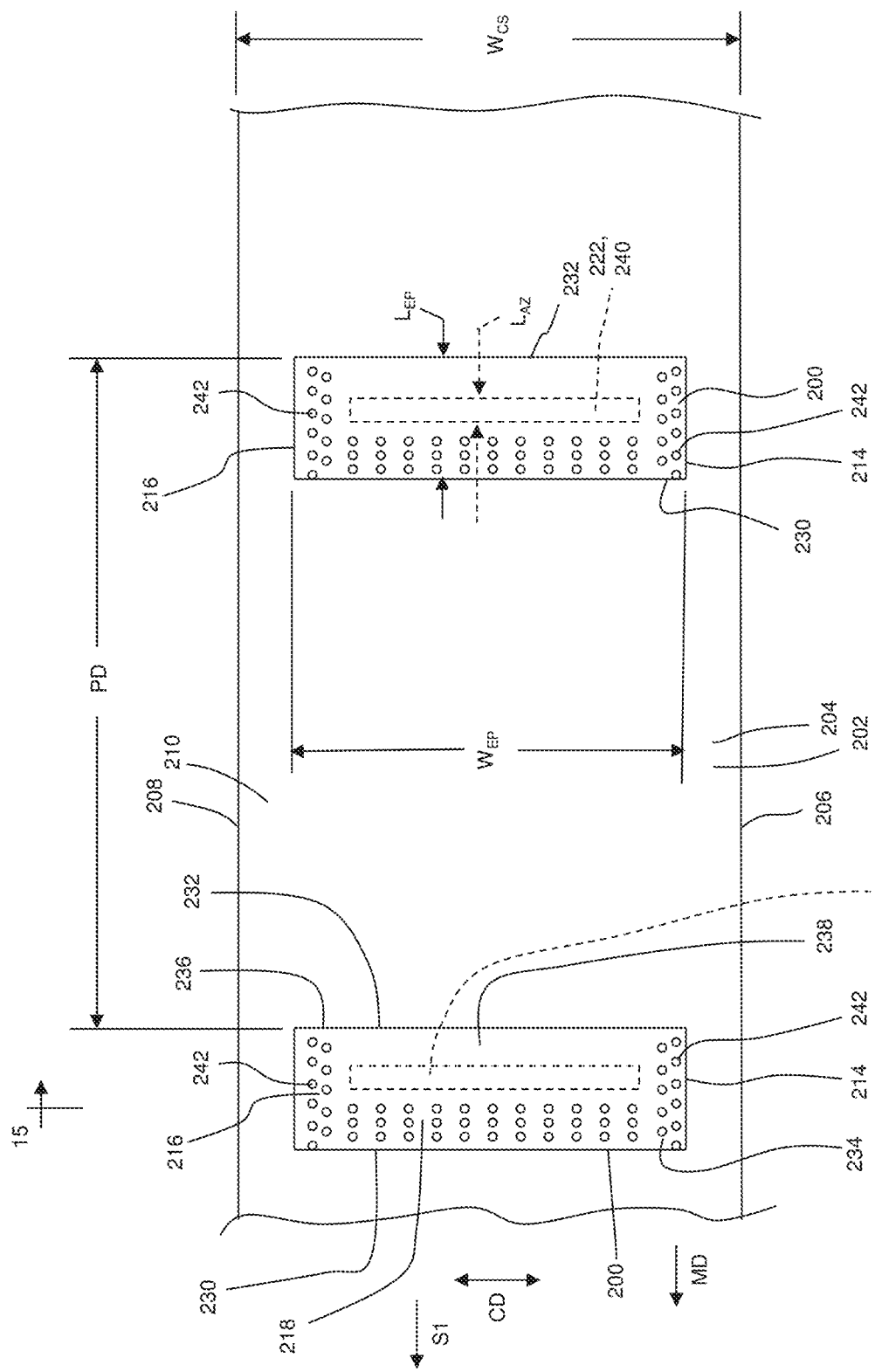
FIG. 14 is a view of a laminate including the elastic part and the carrier substrate taken along section 14-14 in FIG. 4.

In some configurations, the third speed S3 may be equal to the first speed S1 of the advancing carrier substrate 202. In some configurations, the third speed S3 may be less than or greater than the first speed S1 of the advancing carrier substrate 202, and as such, the discrete elastic part may be accelerated or decelerated downstream of the anvil roll 308 from the third speed S3 to the first speed S1 before being combined with the carrier substrate 202. Because the first speed S1 of the carrier substrate is greater than the second speed S2, the discrete elastic parts 200 are accelerated from the second speed S2 to the first speed S1 before bonding with the carrier substrate 202. By accelerating discrete elastic parts 200 from the second speed S2 to the first speed S1, trailing edges 232 (or leading edges 230) of consecutively cut discrete elastic parts 200 may be separated from each other in the machine direction MD by a pitch distance PD, such as shown in FIG. 14, which may correspond with the pitch length PL described above with reference to FIGS. 1A and 1B. The anvil roll 308 may also be configured to apply vacuum pressure to the discrete elastic parts 200 to help hold the discrete elastic parts 200 on the outer circumferential surface 318 as the anvil roll 308 rotates.

It is to be appreciated that the cutting device 304 may be configured in various ways. For example, in some configurations, the blade 314 may be configured such that resulting cut lines and corresponding leading edges 230 and trailing edges 232 of the discrete elastic parts 200 may be straight and/or curved. The cutting device 304 may also be adapted to cut the discrete elastic parts 200 such that material along the cut line adjacent leading edges 230 and trailing edges 232 is fused and/or pressure bonded together. It is also to be appreciated that the positions of the knife roll 306 and anvil roll 308 may be opposite to that which is illustrated in FIG. 4, and as such, the discrete elastic parts 200 may remain on the outer circumferential surface 312 of the knife roll 306 as opposed to the anvil roll 308. It is also to be appreciated that the cutting device 304 may be configured to convey and/or cut the discrete elastic parts 200 in different ways.

Figure 10:
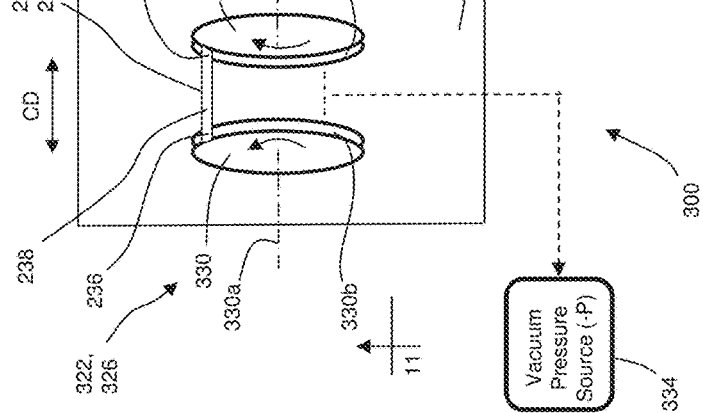
FIG. 10 is a view of the transfer device and bonding device taken along section 10-10 in FIG. 9.

With reference to FIG. 4, the apparatus 300 may include a rotatable transfer device 322 that transfers the discrete elastic parts 200 from the cutting device 304 to a bonding device 324, which in turn, combines the elastic parts 200 with the carrier substrate 202. The transfer device 322 may also be configured to stretch the discrete elastic parts 200 in the cross direction CD. As such, the transfer device 322 may be configured as a spreader mechanism 326, such as shown in FIGS. 9 and 10. With continued reference to FIGS. 4, 9, and 10, the transfer device 322 may be positioned adjacent the anvil roll 308 to define a nip 328 therebetween. As discussed in more detail below, the discrete elastic parts 200 are received from the anvil roll 308 and the spreader mechanism 326 operates to stretch discrete elastic parts 200 in the cross direction CD. The stretched discrete elastic parts 200 are then advanced from the spreader mechanism 326 onto a rotating component of the bonding device 324, which in turn, bonds the stretched discrete elastic parts 200 onto the carrier substrate 202.

Figure 11A:
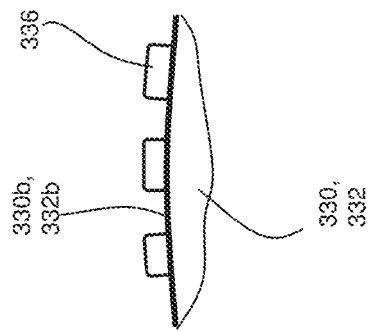
FIG. 11A is a detailed view of radially protruding nubs on an outer rim of a disk.
Figure 11:
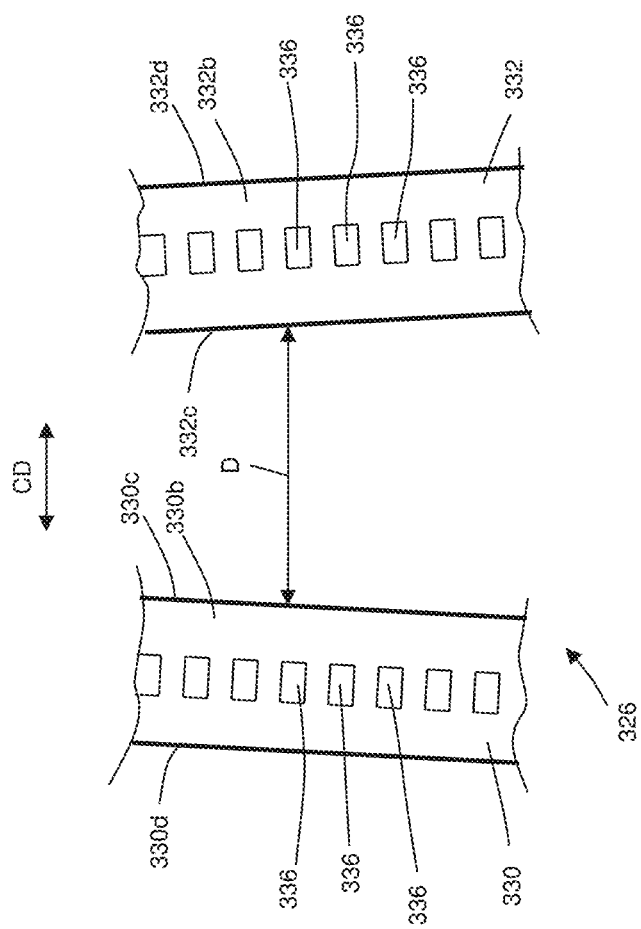
FIG. 11 is a detailed view of the spreader mechanism taken along section 11-11 in FIG. 10.

As shown in FIGS. 9 and 10, the spreader mechanism 326 may include a first disk 330 and a second disk 332, wherein the first disk 330 is displaced from the second disk 332 in the cross direction CD. The first disk 330 is adapted to rotate about an axis of rotation 330a and the second disk 332 is adapted to rotate about an axis of rotation 332a, wherein the first and second disks 330, 332 may rotate in a third direction Dir3 that is opposite the second direction Dir2. As shown in FIG. 11, the first disk 330 includes an outer rim 330b extending axially between an inner edge 330c and an outer edge 330d, and the second disk 332 includes an outer rim 332b extending axially between an inner edge 332c and an outer edge 332d.

Figure 12:
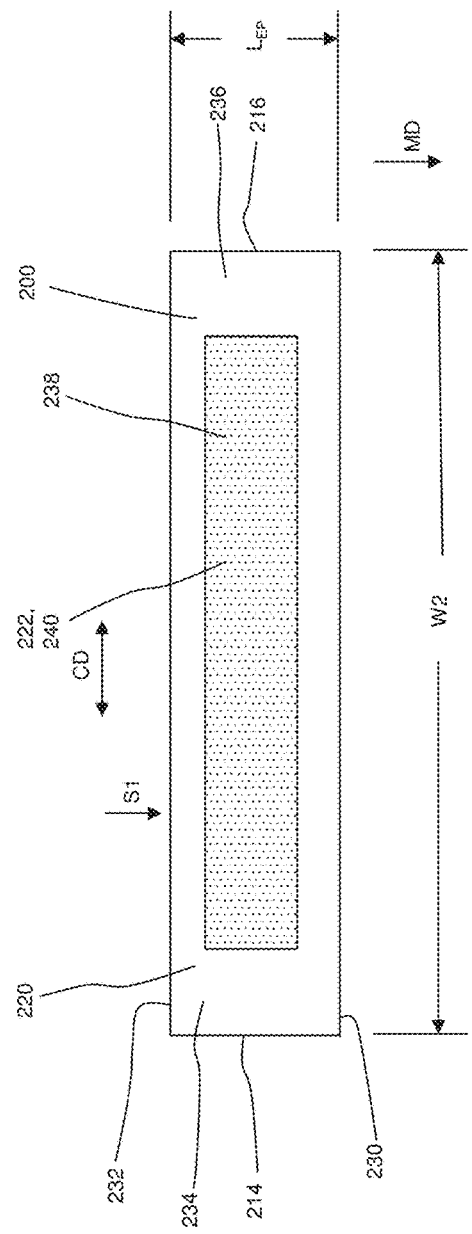
FIG. 12 is a view of a stretched discrete elastic part laid out flat with a zone of adhesive thereon taken along section 12-12 in FIG. 4.

As shown in FIGS. 9-11, the first disk 330 and the second disk 332 are canted relative to each other such that the outer rims 330b, 332b are separated from each other by a distance D that increases from a minimum distance Dmin at a first location to a maximum distance Dmax at a second location. As discussed below, the discrete elastic parts 200 are transferred from the cutting device 304 onto the outer rims 330b, 332b during operation. Because the first and second disks 330, 332 are canted, rotation of the disks 330, 332 causes the rims 330b, 332b to pull on first end region 234 and the second end region 236 of discrete elastic parts 200 and stretch the central regions 238 of the discrete elastic parts 200 in the cross direction CD before the discrete elastic parts 200 are transferred to the bonding device 324. As shown in FIGS. 4, 8, and 12, the spreader mechanism 326 may operate to stretch the discrete elastic parts 200 in the cross direction from a first width W1 to a second width W2 that is greater than the first width W1.

With reference to FIGS. 4, 9, and 10, the disks 330, 332 may also be configured to help grip the opposing first and second end regions 234, 236 of the discrete elastic parts 200 during operation. For example, the first disk 330 and the second disk 332 may each be fluidly connected with a vacuum pressure source 334. As such, vacuum air pressure may be used to help hold the discrete elastic parts 200 onto the rims 330b, 332b during operation. As shown in FIGS. 11 and 11A, the disks 330, 332 may also include nubs 336 that protrude radially outward from the rims 330b, 332b. As such, the nubs 336 may also help prevent the first and second end regions 234, 236 of the discrete elastic parts 200 from sliding along the rims 330b, 332b while stretching the central region 238 of the discrete elastic parts 200. It is also noted that because the first and second end regions 234, 236 of the discrete elastic part 200 are held on the rims 330b, 332b during the stretching operation, the central region 238 of the discrete elastic part 200 is stretched while the first and second end regions 234, 236 may not be stretch or may be stretched to a much lesser degree than the central region 238.

As previously discussed with reference to FIG. 8, the elastic part 200 may include a zone 240 of adhesive 222 that is positioned on the central region 238 of the discrete elastic part 200 and wherein portions of or all of the first end region 234 and the second end region 236 of the second surface 220 of the discrete elastic part 200 may not include any adhesive 222. As shown in FIGS. 4, 9, and 10, once transferred to the transfer device 322, the elastic parts 200 may be oriented such that the first surface 218 may be facing radially outward, and the second surface 220 and the zone 240 of adhesive 222 may be facing radially inward. As such, the arrangement of disks 330, 322 of the spreader mechanism 326 provide the ability to rotatably convey the elastic parts 200 from the cutting device 304 to the bonding device 324 with a zone 240 of adhesive 222 that faces radially inward without having to contact the adhesive 222 with the disks 330, 332.

As discussed above, the cut discrete elastic parts 200 accelerate from the second speed S2 to the third speed S3 on the outer circumferential surface 318 of the anvil roll 308, and in some configurations, the third speed S3 may be less than or greater than the first speed S1 of the advancing carrier substrate 202. Thus, the transfer device 322 may be configured to rotate at a variable angular velocity to accelerate or decelerate the discrete elastic parts 200 to the first speed S1. For example, if the third speed S3 is less than the first speed S1, the transfer device 322 may be configured to receive the discrete elastic part 200 from the anvil roll 308 while the rims 330b, 332b of the first and second disks 330, 332 are moving through the nip 328 at the third speed S3. The angular velocity of the disks 330, 332 may then be changed to accelerate the discrete elastic part 200 to the first speed S1 before transferring the discrete elastic part 200 to the bonding device 324. In another example, if the third speed S3 is greater than the first speed S1, the angular velocity of the disks 330, 332 may be changed to decelerate the discrete elastic part 200 to the first speed S1 before transferring the discrete elastic part 200 to the bonding device 324. In situations where the third speed S3 is equal to the first speed S1, the disks 330, 332 may rotate at a constant angular velocity. It is to be appreciated that the spreader mechanism 326 may be configured in various ways to accommodate a need to rotate at variable angular velocities, such as, for example, disclosed in European Patent Publication No. EP 2260813 B1, which is incorporated by reference herein. The ability to rotate at the transfer device 326 at variable angular velocities may help reduce the need to replace components of the apparatus 300 when assembling absorbent articles 100 of smaller or larger sizes, which in turn, may require a reduction or increase in the pitch distances between consecutively cut discrete elastic parts 200.

As previously mentioned, the rotatable transfer device 322 may be configured to transfer the discrete elastic parts 200 from the cutting device 304 to a bonding device 324. As shown in FIGS. 4, 9, and 10, the bonding device 324 may be positioned adjacent the first and second disks 330, 332 of the spreader device 326 to define a nip 338 therebetween. In some configurations, the first and second disks 330, 332 may be configured to apply positive air pressure, sometimes referred to as blow-off air, to the discrete elastic part 200 adjacent the nip 338 to help remove the discrete elastic parts 200 from the disks 330, 332 during transfer to the bonding device 324. As discussed in more detail below, the discrete elastic parts 200 are received from the spreader mechanism 326 with the central regions 238 stretched in the cross direction CD, and the bonding device 324 transfers and bonds the discrete elastic parts 200 in the stretched state to the advancing carrier substrate 202.

It is to be appreciated that the bonding device 324 may be configured in various ways. For example, as shown in FIGS. 4, 9, and 10, the bonding device 324 may be configured with a pattern roll 340 and a pressing surface 342 adjacent the pattern roll 340 to define a nip 344 therebetween. The pattern roll 340 includes an outer circumferential surface 346 and rotates about an axis of rotation 348, wherein the pattern roll 340 may rotate in a fourth direction Dir4 that is opposite the third direction Dir3. In addition, pattern roll 340 may rotate such that the outer circumferential surface 346 advances at or about the first speed S1. During operation, discrete elastic parts 200 in a stretched state are transferred from the first and second disks 330, 332 to the outer circumferential surface 346 of the pattern roll 340. The pattern roll 340 rotates to advance the stretched elastic parts 200 between the outer circumferential surface 346 of the pattern roll and the advancing carrier substrate 202. In particular, the first surface 218 of the discrete elastic part 200 may be positioned in a facing relationship with and in direct contact with the outer circumferential surface 346 of the pattern roll 340. As such, the zone 240 of adhesive 222 and the second surface of the discrete elastic part 200 may be facing radially outward from the rotation axis 348. The carrier substrate 202 advances to the pattern roll 340 such that the first surface 210 of the carrier substrate 200 is in direct contact with and in a facing relationship with the outer circumferential surface 346 of the pattern roll 340. As the pattern roll 340 rotates, the second surface 220 of the discrete elastic part 200 is positioned in direct contact with and in a facing relationship with the first surface 210 of the carrier substrate 200. The combined discrete elastic part 200 and the carrier substrate 202 advance through the nip 344 between the pattern roll 340 and the pressing surface 342 to mechanically bond the discrete elastic part 200 and the carrier substrate 202 together.

Figure 13A:
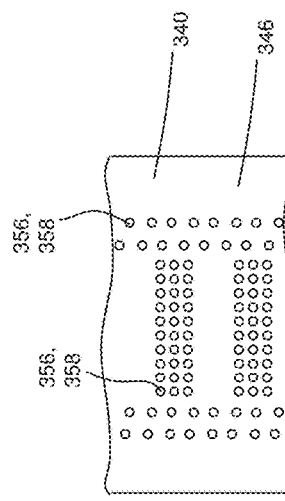
FIG. 13A is a detailed view of a portion of the outer circumferential surface of the pattern roll showing bonding elements from FIG. 13 taken along line 13A-13A.
Figure 13:
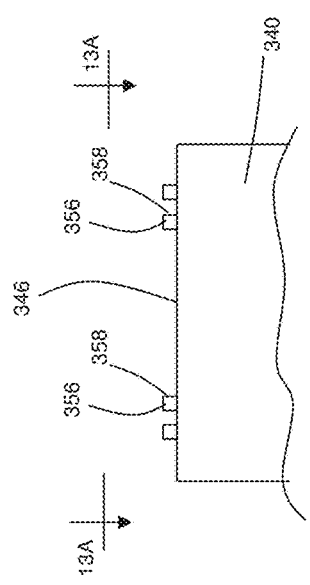
FIG. 13 is a detailed cross sectional view of a pattern roll from FIG. 9 showing bonding elements extending radially outward from an outer circumferential surface taken along line 13-13.

As shown in FIG. 4, the bonding device 324 may be configured as a mechanical bonding device that includes an anvil roll 350. The anvil roll 350 may include an outer circumferential surface 352 and rotates about an axis of rotation 354, wherein the anvil roll 350 may rotate in a fifth direction Dir5 that is opposite the fourth direction Dir4. The outer circumferential surface 352 of the anvil roll 350 may define the pressing surface 342 operating in conjunction with the pattern roll 340. As shown in FIGS. 13 and 13A, the outer circumferential surface 346 of the pattern roll 340 may also comprise one or more bonding surfaces 356 defined by bonding elements 358 extending radially outward. As the pattern roll 340 rotates, the discrete elastic parts 200 and the carrier substrate 200 are advanced between the bonding surfaces 356 and the pressing surface 342 to mechanically bond or weld the elastic part 200 and the carrier substrate 202 together to create bonds 242 between the elastic part 200 and the carrier substrate 202. Heat and/or pressure between the pressing surface 342 and the pattern roll 340 may melt and bond the carrier substrate 202 and the elastic part 200 together in areas supported by the bonding surfaces 356 on the pattern roll 340. As shown in FIG. 14, the mechanical bonds and/or bond regions 242 may have shapes that correspond with and may mirror shapes of the bonding surfaces 356.

Thus, as the laminate 204 advances through the nip 344, the carrier substrate 202 and the discrete elastic part 200 are mechanically bonded or welded together. It is to be appreciated that the bonding device 324 herein may be configured in various ways with various features described herein to bond the discrete elastic parts 200 with the carrier substrate 202. As such, the pattern roll 340 and/or anvil roll 350 may be configured to apply heat and pressure in various ways to perform mechanical bonding, such as for example, the mechanical bonding devices and methods disclosed in in U.S. Pat. Nos. 4,854,984; 6,248,195; 8,778,127; 9,005,392; 9,962,297; and 10,052,237. It is also to be appreciated that the positions of the pattern roll 340 and anvil roll 350 may be opposite to that which is illustrated in FIG. 4, and as such, the discrete elastic parts 200 may be transferred from the transfer device 322 to the outer circumferential surface 352 of the anvil roll 350 as opposed to the pattern roll 340. It is also to be appreciated that one or more components of the bonding device 324 may be configured to operate at constant and/or variable speeds. For example, the pattern roll 340 and/or the anvil roll 350 may be connected with various types of motors, such as servo motors for example, that may rotate the pattern roll 340 and/or the anvil roll 350 at constant and/or variable angular velocities.

In some configurations, the carrier substrate 202 may be partially wrapped around the outer circumferential surface 346 of the pattern roll 340. As such, the bonding device 324 may include one or more rolls that help guide the carrier substrate 202 to and/or from the pattern roll 340. For example, as shown in FIG. 4, the bonding device may include a guide roll 360 that helps to guide the carrier substrate 202 onto the outer circumferential surface 346 of the pattern roll 340 downstream of the nip 338 where the elastic parts 202 are received from the transfer device 322 and upstream of the nip 344 between the pattern roll 340 and the pressing surface 342. The guide roll 360 may also be configured to apply pressure against the carrier substrate 202 and the elastic part 200 to help enhance the bonding of the adhesive 222 of the adhesive zone 240 and the carrier substrate 202.

Figure 4A:
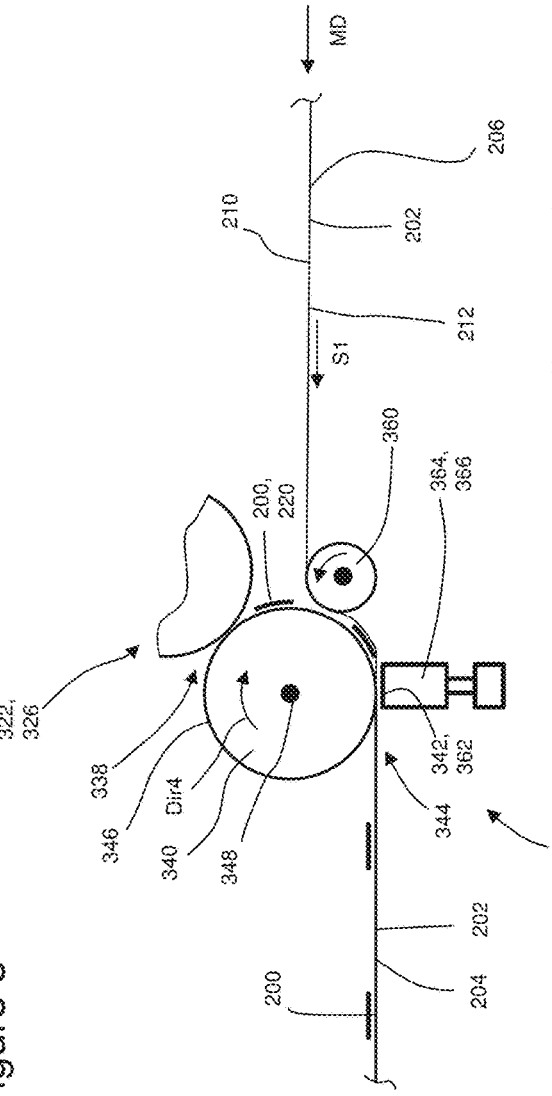
FIG. 4A is a detailed schematic view of a bonding apparatus with a pressing surface comprising an ultrasonic bonding device.

It is to be appreciated that the bonding device 324 may be configured in various ways, such as with heated or unheated pattern rolls, anvil rolls and/or ultrasonic bonding devices. For example, the bonding device 324 schematically shown in FIG. 4A may include the pattern roll 340 and the pressing surface 342 that comprises an energy transfer surface 362 of an ultrasonic bonding device 364. As such, the bonding device 364 may include a horn 366 and may be configured to impart ultrasonic energy to the combined elastic part 200 and the carrier substrate 202 on the pattern roll 340.

It is to be appreciated that aspects of the ultrasonic bonding device 364 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device 364 may be configured as a linear oscillating type sonotrode, such as for example, available from Herrmann Ultrasonic, Inc. In some configurations, the sonotrode may include a plurality of sonotrodes nested together in the cross direction CD. It is also to be appreciated that rotary horns may also be configured to rotate at constant and/or variable angular velocities.

As discussed above, the pattern roll 340 includes bonding elements 358 that extend radially outward to define bonding surfaces 356. In turn, the bonds and/or bond regions 242 between the discrete elastic part 200 and the carrier substrate 202 may have shapes that correspond with and may mirror shape of the bonding surfaces 356. It is to be appreciated that the pattern roll 340 may have various quantities and/or shapes of bonding surfaces 356 and that such bonding surfaces 356 may be positioned in various locations on the pattern roll 340. For example, as shown in FIGS. 13, 13A, 14, and 15, the bonding elements 358 and bonding surfaces 356 may be positioned to correspond with the first end region 234 and the second end region 236 of the discrete elastic part 200. Thus, the bonding device 340 may operate to mechanically bond the first and second end regions 234, 236 of the elastic part 200 without mechanically bonding the stretched central region 238. In some configurations, the bonding elements 358 and bonding surfaces 356 may be positioned such that mechanical bonds 242 are also applied to bond the central region 238 of the discrete elastic part 200 and the carrier substrate 202 together.

The pattern roll 340 may also be configured to apply vacuum pressure to the discrete elastic parts 200 to help hold the discrete elastic parts 200 on the outer circumferential surface 346 as the pattern roll 340 rotates. The vacuum pressure may also help hold the discrete elastic parts 200 in the stretched state while positioned on the pattern roll 340. In addition, the bonding elements 358 and bonding surfaces 356 may also help grip the elastic parts 200 and help hold the elastic parts 200 in the stretched state. In addition, the pattern roll 340 may be configured such to also apply vacuum pressure through the bonding surfaces 356 of the bonding elements 358. Further, the pattern roll 340 may be configured to interface with the first and second disks 330, 332 of the spreader mechanism 326 to help maintain the stretched state of the discrete elastic part 200 during the transfer to the pattern roll 340 at the nip 338. For example, as discussed above, the disks 330, 332 of the spreader mechanism 326 may include various quantities of nubs 336 that protrude radially outward from the rims 330b, 332b, wherein the nubs 336 may help prevent the first and second end regions 234, 236 of the elastic parts 200 from sliding toward each other along the rims 330b, 332b while stretching the discrete elastic parts 200. It is to be appreciated that the nubs 336 may be configured in various shapes and sizes, spacing, and may be constructed from various types of materials. In some configurations, the bonding elements 358 on the pattern roll 340 may be configured to intermesh with the nubs 336 protruding from the rims 330b, 332b of the first and second disks 330, 332. The intermeshing between the nubs 336 and the bonding elements 358 may help the apparatus 300 maintain the stretched state of the discrete elastic part 200 when transferring from the transfer device 322 to the bonding device 324.

Figure 14A:
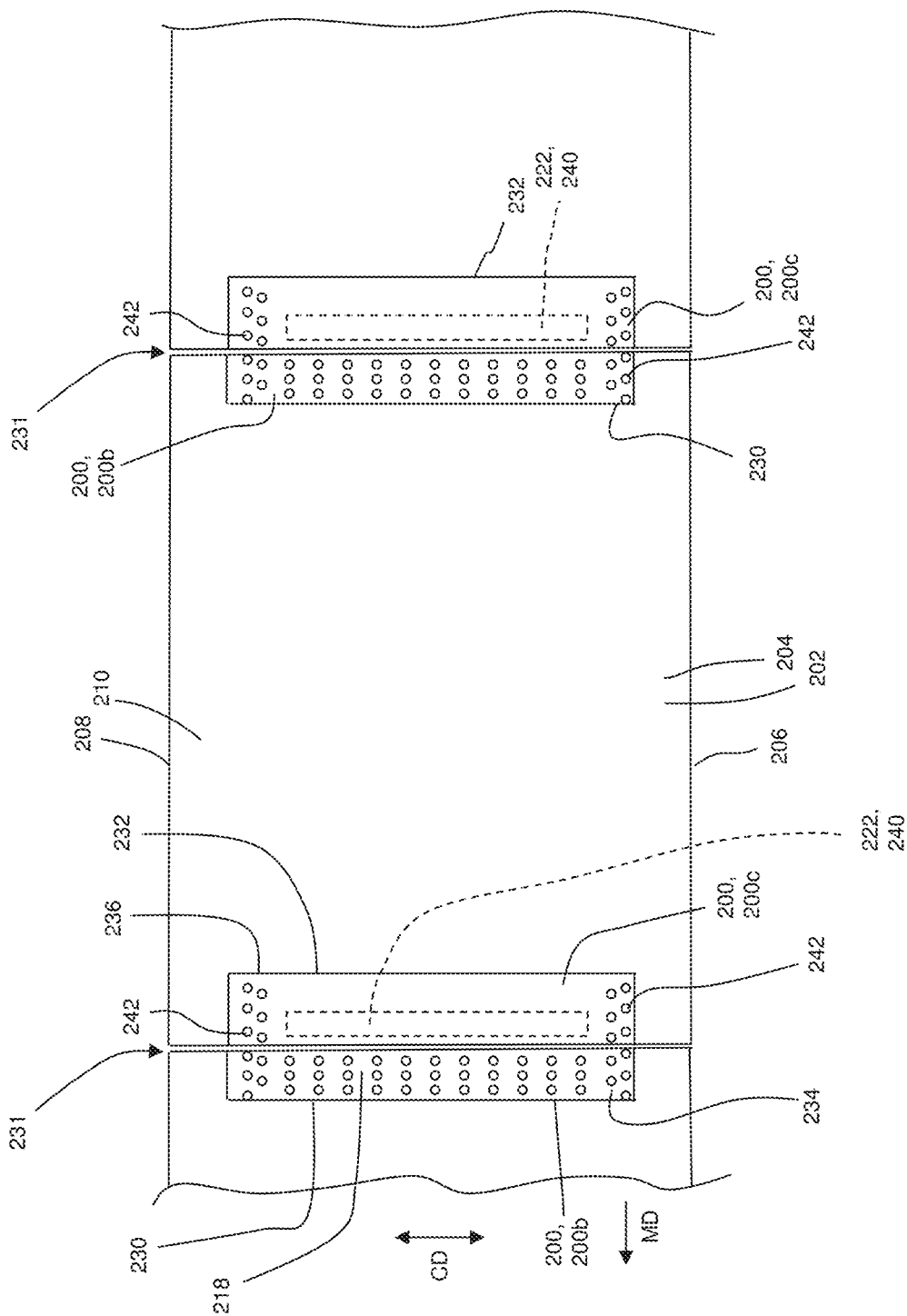
FIG. 14A is a view of the laminate of FIG. 14 including the elastic part and the carrier substrate after being subjected to a final knife cut operation that applies cut lines through the carrier substrate and discrete elastic parts.

As shown in FIG. 4, after the discrete elastic part 200 is bonded with the carrier substrate 202 to create the laminate 204, the laminate 204 may continue to advance in the machine direction MD from the bonding device 324 and may be subjected to additional converting operations, such as cutting, folding, and/or packaging operations. In some configurations, the laminate 204 may define a continuous length of absorbent articles or may be combined with additional substrates and/or components to define a continuous length of absorbent articles. In turn, the continuous length of absorbent articles may be subjected to a final knife cut that separates discrete absorbent articles from the continuous length of absorbent articles. As previously mentioned, the discrete elastic parts 200 may correspond with waist panels 158 on the absorbent articles 100 and the carrier substrate 202 may correspond with a topsheet substrate 138 or backsheet substrate 136. In some configurations, the apparatuses and methods herein may be configured to apply discrete elastic parts 200 as discrete front and/or back waist panels 158. In some configurations, the discrete elastic parts 200 may be applied to the carrier substrate 202, and the discrete elastic parts 200 are subsequently cut during the final knife cut operation into a front waist panel 158a positioned in the front waist region 116 and a back waist panel 158b positioned in the back waist region 118. It is to be appreciated that such final knife cut operation may be configured to apply straight and/or curved cut lines through the carrier substrate 202 and discrete elastic parts 200. For example, FIG. 14A shows a view of the laminate 204 showing elastic parts 200 and the carrier substrate 202 after being subjected to a final knife cut operation that applies cut lines 231 through the carrier substrate 202 and discrete elastic parts 200. As such, the discrete elastic parts 200 may be cut into a first elastic part 200b and a second elastic part 200c. In some configurations, the first elastic part 200b may correspond with a first waist panel 158 positioned in the panel first waist region 116, and the second elastic part 200c may correspond with a second waist panel 158 positioned in the second waist region 118. In some configurations, curved cut line 231 may be adapted to create an umbilical cord notch 233a, such as disclosed in U.S. Pat. No. 8,608,720 and U.S. Patent Publication No. 2017/0246052 A1, both of which are incorporated by reference herein.

It is also to be appreciated that the carrier substrate 202 may include parts, such as laterally extending side panels for example, attached thereto upstream of the bonding device 324. As such, the system 300 may also include devices, such as rails and/or conveyors, to help guide and control the carrier substrate 202, and specifically such laterally extending features, into the bonding device 324 to help prevent unintentional bonding of such features.

As discussed above, the discrete elastic parts may be combined with the carrier substrate adhesive and/or mechanical bonds. It is to be appreciated that the adhesive and mechanical bonds may be configured in various ways. It is also to be appreciated that the zone 240 of adhesive 222 may be applied to define various different shapes and sizes with respect to the discrete elastic part 200 and/or the carrier substrate 202. For example, as shown in FIG. 14, the zone 240 of adhesive 222 may define a length $L_{AZ}$ in the machine direction MD. In some configurations, the length $L_{AZ}$ of the zone 240 of adhesive 222 may extend for less than the entire length $L_{EP}$ of the discrete elastic part 200. In some configurations, the zone 240 of adhesive 222 may extend in the cross direction CD to be coterminous with one of or both the leading edge 230 and the trailing edge 232 of the elastic part 200. In some configurations, the length $L_{AZ}$ of the zone 240 of adhesive 222 may extend the entire length $L_{EP}$ of the discrete elastic part 200 extending from the leading edge 230 to the trailing edge 232.

As discussed above with reference to FIG. 4, the system 300 may include an adhesive applicator device 302 that may be configured to apply adhesive 222 to the continuous elastic substrate 200a upstream of the nip 310 between the knife roll 306 and anvil roll 308. In turn, the discrete elastic parts 200 separated from the continuous elastic substrate 200a may include a zone 240 of adhesive 222 that is adapted to adhesively bond the elastic part 200 with the carrier substrate 202. It is to be appreciated that the zone 240 of adhesive 222 may comprise adhesive 222 applied to the continuous elastic substrate 200a, the elastic part 200, and/or the carrier substrate 202 in various configurations and/or positions in the assembly process. For example, as shown in FIG. 4, the system 300 may include an adhesive applicator device 302a that may be configured to apply adhesive 222 to the discrete elastic part 200 at a position downstream of the nip 310 between the knife roll 306 and anvil roll 308. In another example, shown in FIG. 4, the apparatus 300 may include an adhesive applicator device 302b that deposits adhesive 222 onto the first surface 210 of the carrier substrate 202 to define the zone 240 of adhesive 222 that bonds the elastic part 200 with the carrier substrate 202. It is to be appreciated that the adhesive applicator device 302a may be configured to operate in addition to or in place of the adhesive applicators 302, 302b, and adhesive applicator device 302b may be configured to operate in addition to or in place of the adhesive applicators 302, 302a. It is also to be appreciated that the adhesive applicator devices 302a, 302b may be configured in various ways, such as the adhesive applicator 302 described above, such as for example, as a spray nozzle and/or a slot coating device. It is also to be appreciated that in some configurations, the discrete elastic parts 200 may be combined with the carrier substrate 202 with only mechanical bonds and without the use of adhesive.

Figure 16:
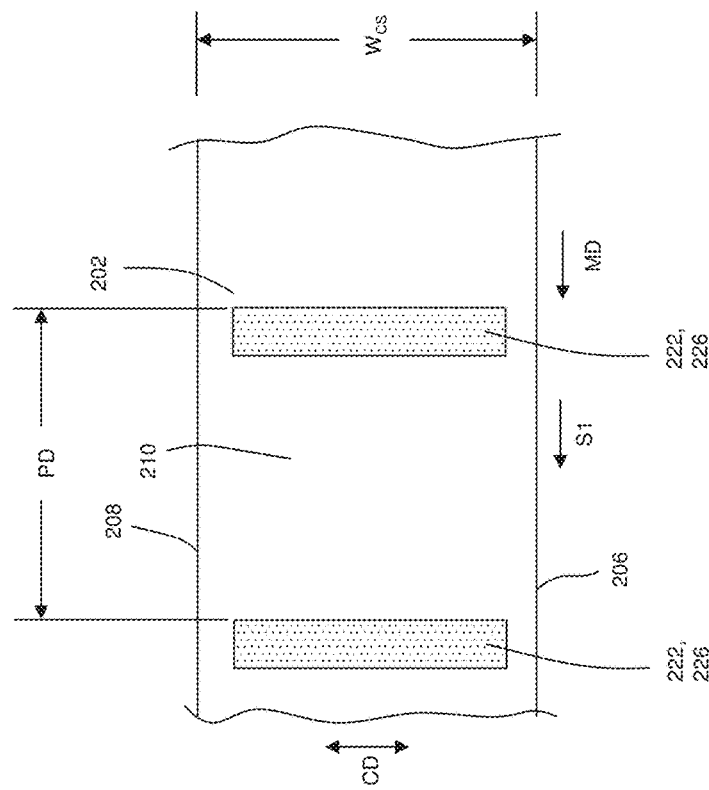
FIG. 16 is a view of the carrier substrate and adhesive taken along section 16-16 in FIG. 4.
Figure 15:
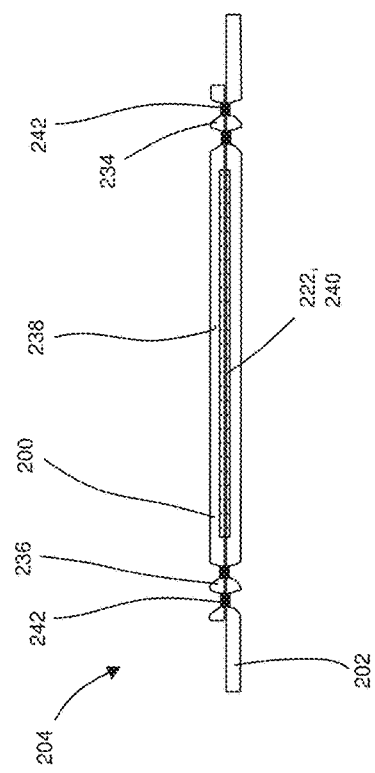
FIG. 15 is a view of the laminate including the elastic part and the carrier substrate taken along section 15-15 in FIG. 14.

In accordance with the above discussion with regard to the various shapes and sizes of the zones 240 of adhesive 222, it is to be appreciated that adhesive 222 may be applied to the continuous elastic substrate 200a and/or the carrier substrate 202 in various ways to define the zones 240 of adhesive 222. For example, as discussed above with reference to FIGS. 4 and 7, adhesive 222 may be applied to the continuous elastic substrate 200a to define a region 224 of adhesive 222 in discrete patches 226 separated from each other in on the continuous elastic substrate 200a in the machine direction MD. In another example, the adhesive 222 may be applied to the second surface 220 of the continuous elastic substrate 200a to extend continuously in the machine direction MD and/or the cross direction CD. In another example, shown in FIG. 16, the adhesive 222 may be applied to the first surface 210 of the carrier substrate 202 in discrete patches 226 separated from each other on the carrier substrate 202 in the machine direction MD. It is to be appreciated that adhesive 222 may be applied to the continuous elastic substrate 200a, the elastic part 200, and/or the carrier substrate 202 in shapes and sizes that define the zones 240 of adhesive 222 that bond the elastic parts 200 and the carrier substrate 202 together. The discrete patches 226 of adhesive 222 may be separated from each other on the carrier substrate 202 in the machine direction MD by the pitch distance PD.

It is also to be appreciated that the waist panels 158 herein may be assembled in various ways, such as for example, the continuous elastic substrate and the discrete elastic parts as disclosed in U.S. Pat. Nos. 6,572,595; 6,830,800; 7,087,287; and 7,803,244; and U.S. Patent Publication Nos. 2018/0042778 A1; 2018/0042787 A1; 2018/0042779 A1; and 2018/0042780 A1, and U.S. patent application Ser. Nos. 16/864,267; 16/864,292; 62/855,001; 62/930,181; 62/930,198; and 62/930,808, which are all incorporated by reference herein. For example, FIGS. 17A-17D show various schematic views of an apparatus 500 operating to assemble a continuous elastic substrate 200a from which the discrete elastic parts 200 may be cut from, such as discussed above. It is to be appreciated that the continuous elastic substrate 200a and the discrete elastic parts 200 herein may be configured in various ways and may include one or more elastic materials, such as for example, elastic film and/or strands. For example, the continuous elastic substrate 200a and the discrete elastic parts 200 may be configured as a single layer of elastic film. In some configurations, the continuous elastic substrate 200a and the discrete elastic parts 200 may be configured as a laminate of two more substrates. For example, the continuous elastic substrate 200a and the discrete elastic parts 200 may be configured as an elastic film bonded in between two or more nonwoven substrates and/or may be bonded with one or more nonwoven substrates. For example, the continuous elastic substrate 200a and the discrete elastic parts 200 may be configured as a bi-laminate with an elastic film bonded with a single nonwoven substrate. In another example, the continuous elastic substrate 200a and the discrete elastic parts 200 may be configured as an elastic film bonded between two or more substrates, wherein the substrates may comprise nonwovens. It is also to be appreciated that nonwoven substrates of the elastic substrate 200a and discrete elastic parts 200 may be of the same or different material and/or basis weights. In some configurations, one more nonwoven substrates of the elastic substrate 200a and discrete elastic parts 200 may be of the same or different material and/or basis weights as one more nonwoven substrates of the carrier substrate 202.

It is also to be appreciated that the continuous elastic substrate 200a and the discrete elastic parts 200 may be assembled in various ways, such as for example, as disclosed in U.S. Pat. Nos. 6,572,595; 6,830,800; 7,087,287; and 7,803,244; and U.S. Patent Publication Nos. 2018/0042778 A1; 2018/0042787 A1; 2018/0042779 A1; and 2018/0042780 A1, which are all incorporated by reference herein. For example, FIGS. 17A-17D show various schematic views of an apparatus 500 operating to assemble a continuous elastic substrate 200a from which the discrete elastic parts 200 may be cut from, such as discussed above.

Figure 17A:
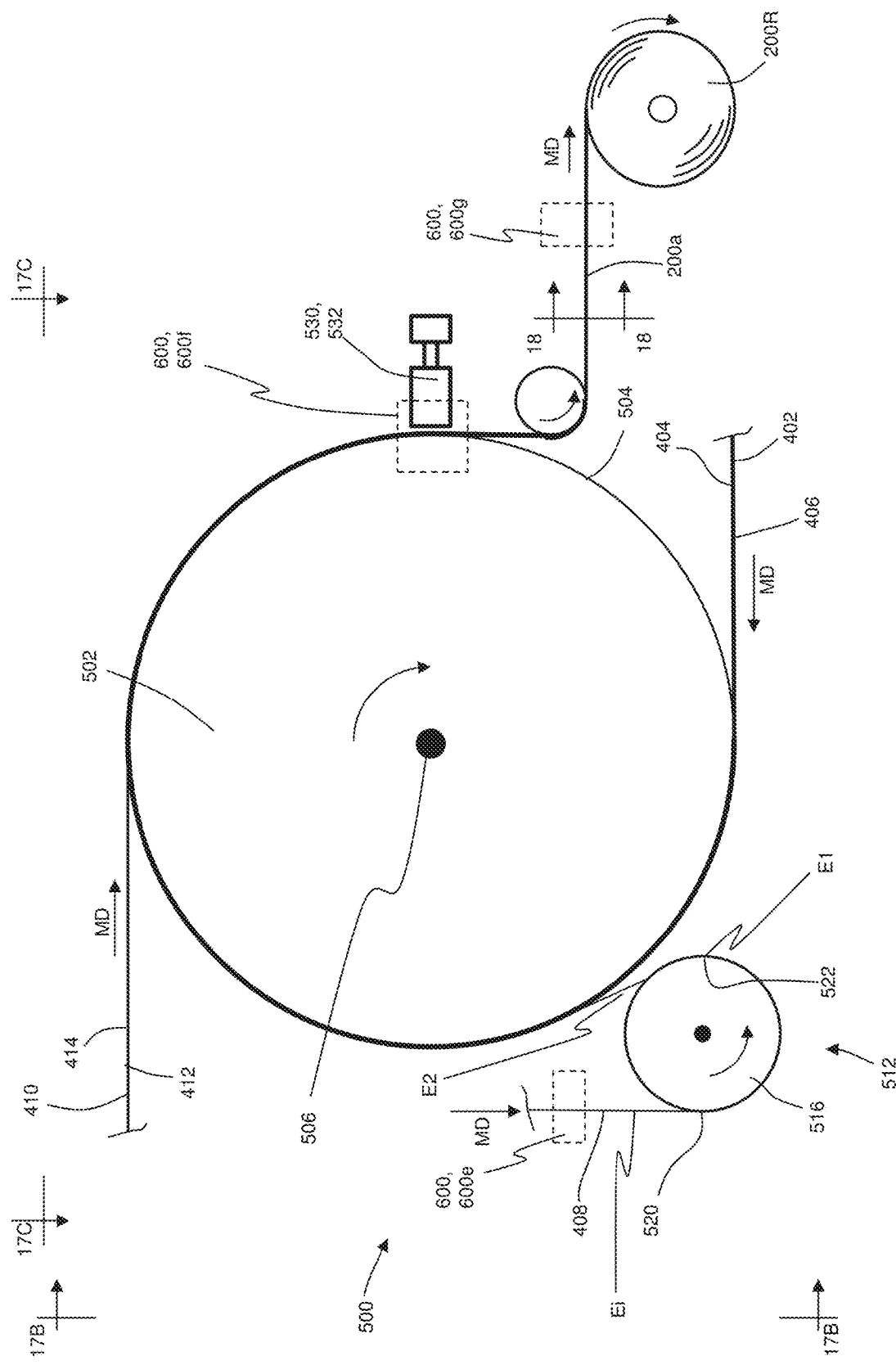
FIG. 17A is a schematic side view of an apparatus operating to assemble an elastic substrate.
Figure 17B:
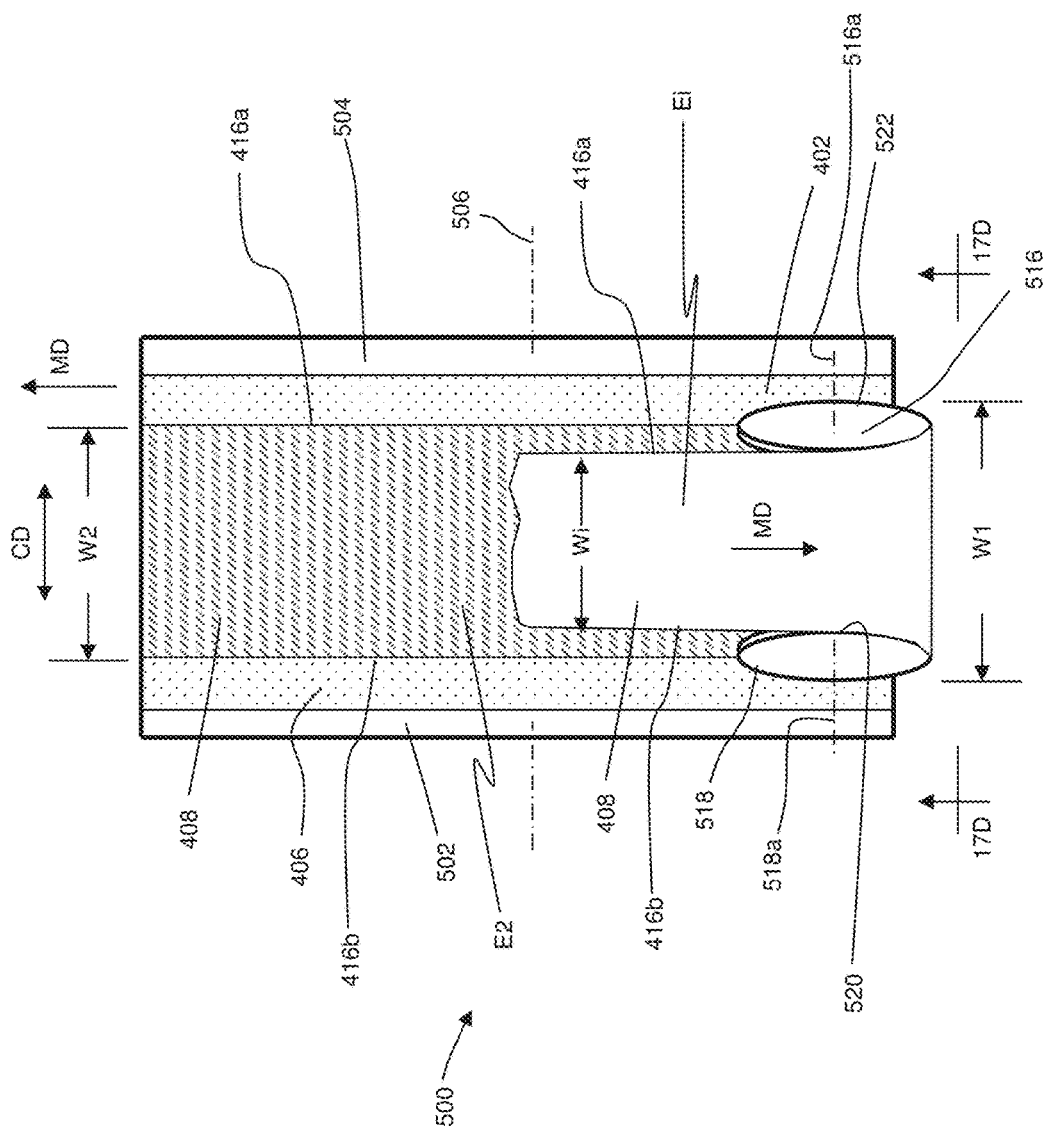
FIG. 17B is a left side view of the apparatus from FIG. 17A taken along line 17B-17B.
Figure 17C:
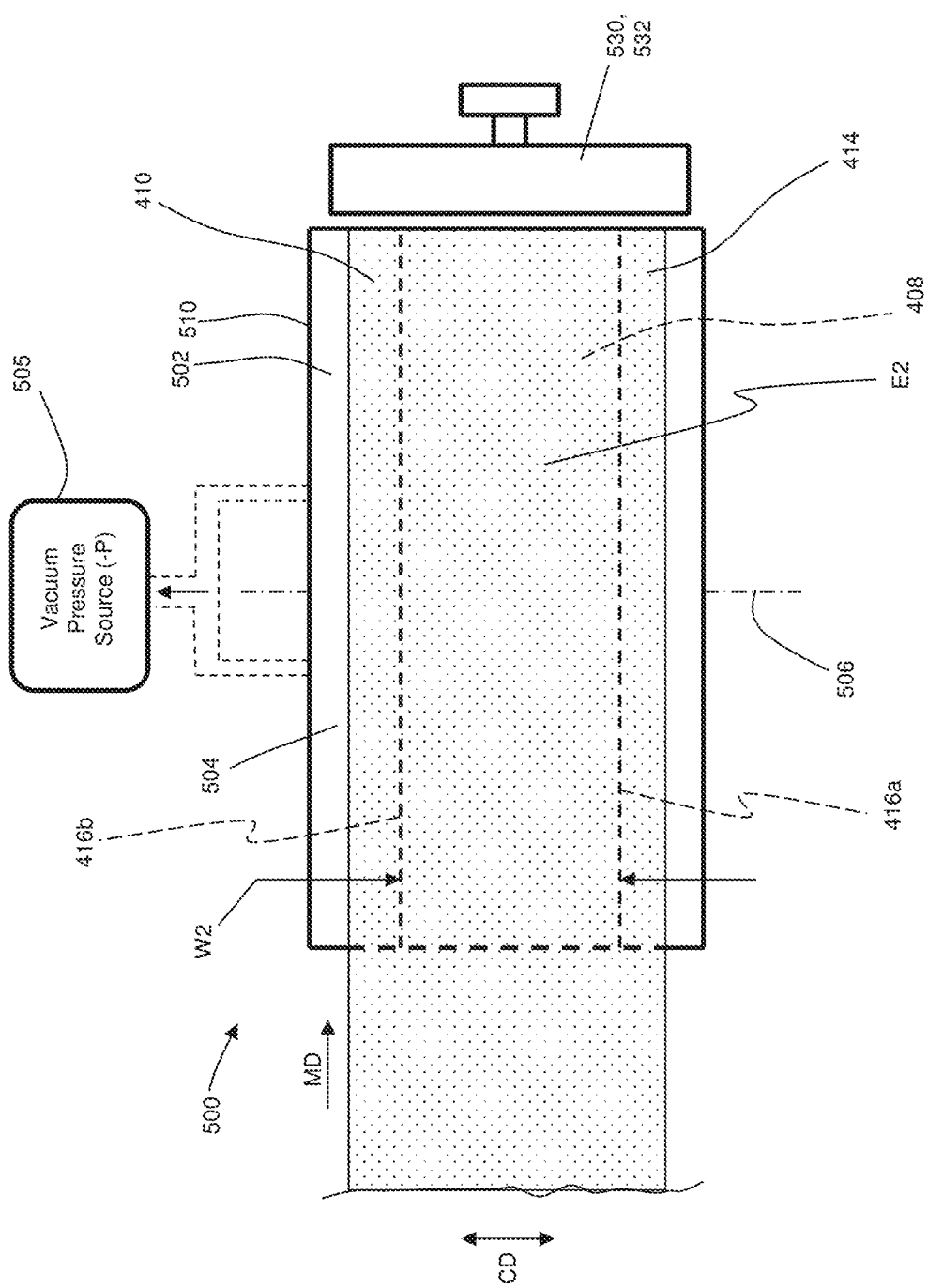
FIG. 17C is a top side view of the apparatus from FIG. 17A taken along line 17C-17C.

As shown in FIGS. 17A-17C, a first substrate 402 advances in a machine direction MD onto a rotating anvil 502. More particularly, the first substrate 402 includes a first surface 404 and an opposing second surface 406, and the first substrate 402 advances to wrap the first surface 404 onto an outer circumferential surface 504 of the rotating anvil 502. During the assembly process, a spreader mechanism 512 stretches an elastic film 408 by stretching the elastic film 408 to a first elongation in the cross direction CD. And the stretched elastic film 408 is positioned into contact with the second surface 406 of the first substrate 402. In turn, the elastic substrate 200a may be formed by ultrasonically bonding the first substrate 402 and the elastic film 408 together with a second substrate 410 on the anvil 502. More particularly, the second substrate 410 includes a first surface 412 and an opposing second surface 414, and the second substrate 410 advances to position the first surface 412 in contact with the elastic film 408 and the second surface 406 of the first substrate 402.

With continued reference to FIGS. 17-17C, as the anvil 502 rotates, the first substrate 402, the elastic film 408, and the second substrate 410 are advanced between the outer circumferential surface 504 of the anvil 502 and one or more ultrasonic devices 530 adjacent the anvil 502. It is to be appreciated that the ultrasonic device 530 may include a horn 532 and may be configured to impart ultrasonic energy to the combined substrates and elastic films on the anvil 502. It is to be appreciated that aspects of the ultrasonic bonding device 530 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device 530 may be configured as a linear oscillating type sonotrode, such as for example, available from Herrmann Ultrasonic, Inc. In some configurations, the sonotrode may include a plurality of sonotrodes nested together in the cross direction CD. In turn, the ultrasonic horn 532 bonds the first substrate 404, the elastic film 408, and the second substrate 410 together to form the elastic substrate 200a.

As shown in FIGS. 17A and 18, the elastic substrate 200a may then advance from the anvil 502 and may be accumulated, such as for example, by being wound onto a roll 200R or being festooned in a container. It is to be appreciated that the elastic substrate 200a may be wound onto a roll 200R in a fully stretched, partially stretched, or fully relaxed state. The accumulated elastomeric substrate 200a may be stored and/or moved to a location for incorporation into an absorbent article assembly process wherein the elastomeric substrate 200a may be converted into an absorbent article component, such as discussed above. It is also to be appreciated that the elastic substrate 200a may advance from the anvil 502 and directly to absorbent article assembly processes. FIG. 19 also shows the elastic substrate 200a in a relaxed state wherein the central region 408c of the elastic film 408 is contracted in the cross direction CD. It is to be appreciated that the apparatus 500 may be configured to assemble elastic substrates 200a with a single lane of elastic film 408 and may also be configured to assemble elastic substrates 200a with multiple lanes of elastic film 408 separated from each other in the cross direction. In turn, the elastic substrate 200a may be cut along the machine direction MD between such lanes of elastic films 408 to create multiple individual elastic substrates 200a.

During the ultrasonic bonding process, it is to be appreciated that bonds imparted into the elastic substrate 200a from the ultrasonic horn 532 may correspond with patterns and/or shapes defined by a plurality of pattern elements extending radially outward from the outer circumferential surface 504 of the anvil 502. It is to be appreciated that the elastic substrate 200a may include various portions of components bonded together in various ways and with differing or identical bond patterns. For example, the elastic film 408 may be bonded together with the first and/or second substrates 402, 410, and the first substrate 402 may be bonded directly to the second substrate 410 in areas of the elastic substrate 200a. In some configurations, the first and second substrates 402, 410 may be bonded directly to each other through apertures in the elastic film, wherein such apertures may be formed during the bonding process. In some configurations, the elastic film 408 can be involved, or participate, in the bonding between the first and second substrates 402, 410, wherein "involved" can mean that the elastic film can, to some extent, be in intimate contact with, and possibly partially merged with, one or both the first and second substrates 402, 410. The involvement may be due to actual melt bonding about the perimeter of a bond site or may be due to mechanical interaction, such as by entanglement of a fibrous elastic layer between fibrous nonwoven layers also about the perimeter of bond site. It is to be appreciated that the apparatus 500 may be adapted to create various types of bond configurations, such as disclosed, for example, in U.S. Pat. Nos. 6,572,595; 6,830,800; 7,087,287;

and 7,803,244; and U.S. Patent Publication Nos. 2018/0042778 A1; 2018/0042787 A1; 2018/0042779 A1; and 2018/0042780 A1, which are all incorporated by reference herein.

Figure 17D:
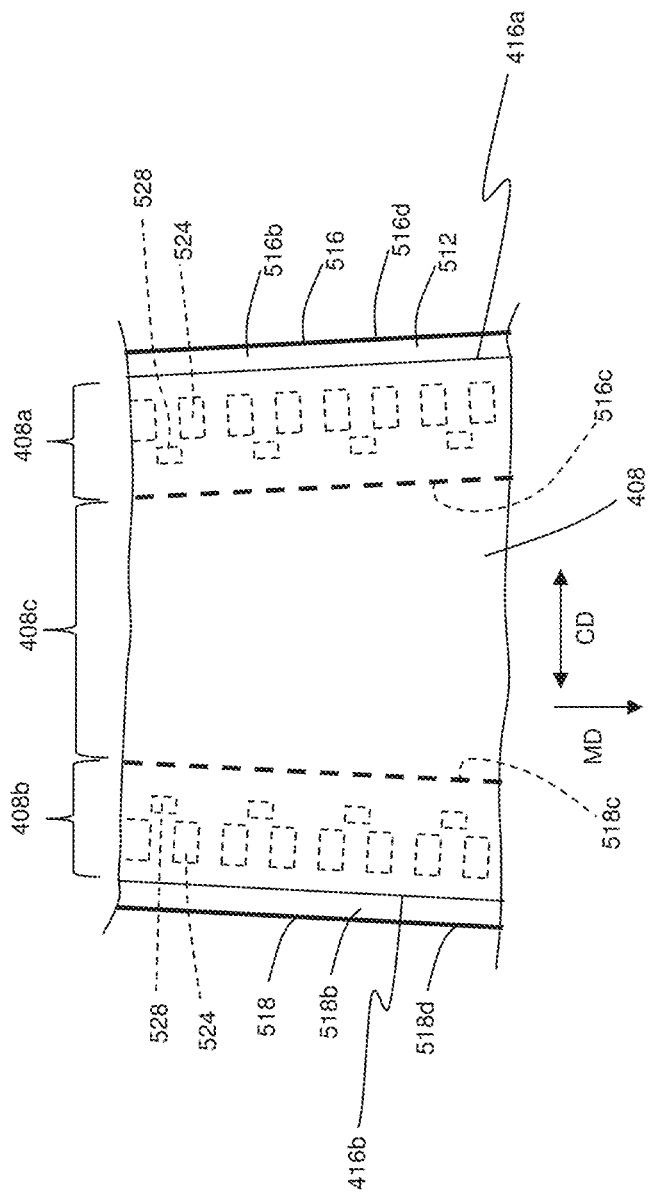
FIG. 17D is a detailed view of an elastic material advancing on a spreader mechanism from FIG. 17B taken along line 17D-17D.

As previously mentioned, the spreader mechanism 512 stretches the elastic film 408 to a first elongation E1 in the cross direction CD. With particular reference to FIGS. 17A and 17D, the elastic film 408 includes a first edge 416a and a second edge 416b separated from the first edge 416a in the cross direction CD. In addition, the elastic film 408 includes a first edge region 408a adjacent the first edge 416a and a second edge region 408b adjacent the second edge 416b. The first edge region 408a is separated from the second edge region 408b in the cross direction CD by a central region 408c. As shown in FIGS. 17A and 17B, the elastic film 408 may define an initial width Wi in the cross direction CD between the first edge 416a and the second edge 416b upstream of the spreader mechanism 512. The elastic film 512 advances in a machine direction MD onto the spreader mechanism 512 at a first location 520. It is to be appreciated that elastic film 408 may be at the initial width Wi in the cross direction CD while advancing onto the spreader mechanism 512. It is also to be appreciated that the elastic film 408 may be in a relaxed state upstream of the spreader mechanism 512.

As shown in FIGS. 17B and 17D, the first edge region 408a of the elastic film 408 advances onto an outer rim 516b of a first disk 516 of the spreader mechanism 512, and the second edge region 408b advances onto an outer rim 518b of a second disk 518. In addition, the outer rim 516b of the first disk 516 may extend axially between an inner edge 516c and an outer edge 516d, and the outer rim 518b of the second disk 518 may extend axially between an inner edge 518c and an outer edge 518d. The outer rims 516b, 518b of the first and second disks 516, 518 of the spreader mechanism 512 may include channels 524 fluidly connected to a vacuum pressure source and may include radially protruding nubs 528. Thus, as shown in FIG. 17D, the first edge region 408a of the elastic film 408 may be held in position on the outer rim 516b with vacuum air pressure in the channels 524 and with the radially protruding nubs 528. Similarly, the second edge region 408b of the elastic film 408 may be held in position on the outer rim 518b with vacuum air pressure in the channels 524 and with the radially protruding nubs 528.

With continued reference to FIGS. 17B and 17D, the first disk 516 and the second disk 518 are canted. Thus, as the first disk 516 and the second disk 518 of the spreader mechanism 512 rotate, the elastic film 408 is stretched in the cross direction CD while advancing from the first location 520 or downstream of the first location 520 toward a second location 522. Thus, as shown in the FIGS. 17A, 17B, and 17D, the spreader mechanism 512 may stretch the elastic film 408 in the cross direction CD from the initial width Wi (and an initial elongation Ei) to a first width W1 (and a first elongation E1) in the cross direction CD, wherein W1 is greater than Wi and wherein E1 is greater than Ei. In some configurations, the elastic film 408 may be consolidated to a second width W2 (and second elongation E2), wherein W2 is less than W1 and wherein E2 is less than E1. It is to be appreciated that the elastic film 408 remains stretched at the second width W2 (and second elongation E2). It is also to be appreciated that the elastic film 408 may be in a relaxed state at the initial width Wi (and initial elongation Ei), and as such, the second width W2 may be greater than the initial width Wi and the second elongation E2 may be greater than the initial elongation Ei. In configurations where the elastic film is not consolidated, W2 may be equal to W1 and E2 may be equal to E1.

In some configurations, when the spreader mechanism includes canted disks, the first and second edge regions 408a, 408b of the elastic film 408 may be held in position on the outer rims 516b, 518b of the disks 516, 518. And as such, some portions of the first and second edge regions 408a, 408b may remain unstretched in the cross direction CD as the first and second disks 516, 518 rotate. Thus, as the first disk 516 and the second disk 518 of the first spreader mechanism 512 rotate, the central region 408c of the elastic film 408 is stretched in the cross direction CD.

As shown in FIG. 17A-17D, the elastic film 408 advances from the spreader mechanism 512 downstream of the second location 522 to the anvil 502, and onto the second surface 406 of the first substrate 402 on the anvil 502. And as the anvil 502 rotates, the second substrate 410 advances onto anvil 502 to position the first surface 412 in contact with elastic film 408 and the second surface 406 of the first substrate 402 to form an elastic substrate 200a and the first substrate 402, elastic film 408, and second substrate 410 are bonded together.

With continued reference to FIGS. 17A and 17B, the outer circumferential surface 504 of the anvil 502 may be fluidly connected with a vacuum source 505, and as such, vacuum air pressure may be applied to the first substrate 402 on the anvil 502. For example, the outer circumferential surface 504 of the anvil roll 502 may include a plurality of apertures fluidly connected with the vacuum pressure source. When the first substrate 402 is configured as a porous substrate, such as a nonwoven, vacuum air pressure may also be applied to the elastic film 408 on the anvil 502, and as such, may help maintain the stretched condition of the of the elastic film 408 while on the anvil 502. In some configurations, adhesive on a nonwoven may also help decrease the porosity of the nonwoven, which in turn, may enhance the ability of the vacuum air pressure to help maintain components in a stretched state.

As mentioned above, the elastic substrate 200a and elastic parts 200 may include nonwoven substrates that may be of the same or different material and/or basis weights. For example, the first substrate 402 and the second substrate 410 referred to above with reference to FIGS. 17A-19 may be configured as nonwoven substrates. As such, the first substrate 402 and the second substrate 410 of the elastic substrate 200a and elastic parts 200 may be the same or different types of nonwovens and/or may have the same or different basis weights. In addition, the carrier substrate 202 may include one or more nonwoven substrates. As such, the first substrate 402 and/or the second substrate 410 of the elastic substrate 200a and elastic parts 200 may be the same or different types of nonwovens and/or may have the same or different basis weights as a nonwoven substrate of the carrier substrate 202. In addition, the nonwoven substrates of elastic substrate 200a and elastic parts 200, such as the first substrate 402 and/or the second substrate 410 for example, may include nonwoven substrates having the same or different fiber orientations as a nonwoven substrate of the carrier substrate 202. In turn, the elastic part 200 configured as a waist panel 158 and a carrier substrate 202 configured as a topsheet or backsheet in an absorbent article may each include nonwoven substrates that are the same or different types of nonwovens and/or may have the same or different basis weights and/or may have the same or different fiber orientations.

As previously mentioned, apparatuses and methods to assemble the waist panels and/or bond the waist panels with other absorbent article components may be adapted to assemble absorbent articles 100 with first waist panels 158a and second waist panels 158b that include structural features or morphological features that impart different stretch characteristics to the first and second waist panels 158a, 158b.

For example, with reference to FIG. 4, the apparatus 300 may include one or more transformation apparatuses 600 that may be adapted to modify the elastic substrate 200a, elastic part 200, the carrier substrate 202, and/or the laminate 204 to create morphological differences that result in morphological differences between the first waist panel 158a and the second waist panel 158b. The transformational apparatuses 600 are generically represented in FIG. 4 as dashed line rectangles. It is to be appreciated that the transformational apparatuses 600 may be adapted to form various types of morphological features, such as embossing, apertures, slits, melted material, compressed material, plastic deformations, folds, adhesive bonds, and/or pressure bonds and in various ways, such as for example, by the application ultrasonic energy, laser energy, pressure, heat, adhesive, folds, and or cuts. It is to be appreciated that morphological features may also include size differences between discrete elastic parts 200, such as for example, different machine direction MD lengths. As shown in FIG. 4, the apparatus 300 may include a transformational apparatus 600a upstream of nip 310 that may be adapted to impart morphological features to the elastic substrate 200a. In some configurations, a transformational apparatus may be downstream of nip 310 that may be adapted to impart morphological features to the elastic part 200. A transformational apparatus 600b may be positioned upstream of nip 344 that may be adapted to impart morphological features to the carrier substrate 202. A transformational apparatus 600c may be positioned downstream of nip 344 that may be adapted to impart morphological features to the laminate 204. With continued reference to FIG. 4, the bonding apparatus 324 may also be configured as a transformational apparatus 600d that may be adapted to impart morphological features to the elastic part 200 and/or the carrier substrate 202 during bonding at the nip 344.

In another example, with reference to FIG. 17A, the apparatus 500 may include one or more transformational apparatuses 600 that may be adapted to modify the first substrate 402, the second substrate 410, the elastic film 408, and/or the assembled elastic substrate 200a. The transformational apparatuses 600 are generically represented in FIG. 17A as dashed line rectangles. As discussed above, the transformational apparatuses 600 may be adapted to form various types of morphological features, such as embossing, apertures, slits, melted material, compressed material, plastic deformations, folds, adhesive bonds, and/or pressure bonds and in various ways, such as for example, by the application ultrasonic energy, laser energy, pressure, heat, adhesive, folds, and or cuts. As shown in FIG. 17A, the apparatus 500 may include a transformational apparatus 600f upstream of the spreader mechanism 512 that may be adapted to impart morphological features to the elastic film 408. In some configurations, a transformational apparatus may be downstream of spreader mechanism 512 that may be adapted to impart morphological features to the stretched elastic film 408. With continued reference to FIG. 17A, the anvil 502 and/or the horn 530 may also be configured as a transformational apparatus 600f that may be adapted to impart morphological features to the elastic film 408, the first substrate 406, and/or the second substrate 410 during bonding operations. A transformational apparatus 600g may be positioned downstream of the horn 530 that may be adapted to impart morphological features to the elastic laminate 200a.

It is also to be appreciated that the processes and/or apparatuses herein may be configured with additional features, such as splicing operations, to help avoid having to stop assembly process operations in order to replenish material supplies. In some configurations, the apparatuses 300 discussed herein may be configured to operate with apparatuses that are configured to provide an uninterrupted supply of continuous elastic substrate 200a. For example, during operation, a replacement supply of a continuous elastic substrate 200a may be spliced to a current supply of continuous elastic substrate 200a being used in assembly operations before the current supply is completely depleted.

It is to be appreciated that various types of splicing operations may be used to replenish the supply of a continuous elastic substrate 200a. For example, some splicing operations may be configured to apply a strip of splicing tape to connect a replacement continuous elastic substrate 200a to a nearly depleted elastic substrate 200a to help avoid supply interruptions. As discussed above, the continuous elastic substrate 200a may advance through a cutting device 304 that separates the continuous elastic substrate 200a into discrete elastic parts 200. In addition, a transfer device 322 and/or bonding device 324 may further subject the discrete elastic parts 200 to cross directional stretching and/or bonding operations. However, some splicing tape material may not be stretchable and/or may not be conducive to bonding operations. In turn, discrete elastic parts 200 connected with splicing tape may undesirably disrupt operations of stretching and/or bonding processes. As such, some apparatuses 300 may be configured to remove discrete elastic parts 200 with splicing tape attached thereto from assembly operations before such undesired process disruptions may occur. In some examples, splicing operations may be configured to utilize stretchable splicing tape and/or other materials more conducive to various assembly operations to help prevent unintended assembly process disruptions and/or eliminate the need to remove elastic parts 200 with splicing tape attached thereto.

Some splicing operations may be configured to weld or otherwise bond a replacement supply of a continuous elastic substrate 200a to a current supply of continuous elastic substrate 200a being used in assembly operations without the need to use splicing tape. Such welding operations may utilize hot-wire or ultrasonic apparatuses to create a thermal splice. The thermal splice process may both cut and weld the materials together. In some configurations, thermal splices may be applied so as to maintain some stretch properties, which may allow discrete elastic parts 200 with such thermal splices to advance through cross directional stretching and/or bonding operations without disrupting such operations.

As discussed above, it is to be appreciated that the continuous elastic substrate 200a and the discrete elastic parts 200 herein may be configured in various ways and may include one or more elastic materials, such as for example, elastic film and/or strands. In some configurations, the continuous elastic substrate 200a and the discrete elastic parts 200 may comprise a single layer of elastic film. In some configurations, the continuous elastic substrate 200a and the discrete elastic parts 200 may comprise a laminate of two more substrates, such as an elastic film bonded with one or more nonwoven substrates. When the continuous elastic substrate 200a is configured to comprise an elastic film bonded with one or more consolidated nonwovens, a thermal splice may be configured to melt the layers of both film and nonwoven to create a weld that traps consolidations of the nonwoven materials. In turn, the cross directional stretching process may stretch the elastic part 200 such that the weld may also extend in the cross direction by partially failing a part of the weld that has trapped the consolidated nonwoven, sometimes referred to as "popping the weld." Depending on various splicing process parameters, such as for example weld time, dwell time, and quench time and various material properties, such as for example basis weight, fiber type, and plastic characteristics, the cross directional forces necessary to pop and stretch the weld may vary. In some examples, an ultrasonic splicing apparatus including a relatively sharp cutting anvil may be configured to produce a weld that has a relatively low cross directional force required to pop and stretch. In particular, a relatively smaller overall weld may be produced when a sharp angle of the anvil may penetrate through and burst fibers in the materials without causing a relatively large melt zone, while at the same time allowing the film to weld together, resulting in a splice that may be relatively easier to stretch in the cross direction CD with reduced and/or no popping required.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a first waist region, a second waist region, and a crotch region disposed between the first and second waist regions;
   a first waist edge, a second waist edge, a first longitudinal side edge; and a second longitudinal edge;
   a chassis comprising a topsheet, a backsheet, and an absorbent core positioned between the topsheet and the backsheet;
   leg gasketing elements extending from the first waist region to the second waist region;
   a first waist panel comprising an inboard lateral edge, an outboard lateral edge, and two longitudinal edges, the first waist panel comprising a first elastic film comprising a first end region separated from a second end region by a central region, wherein the central region of the first elastic film is bonded with a first nonwoven in a stretched state and wherein the first and second end regions are bonded with the first nonwoven in unstretched states, and wherein the first waist panel is connected with the chassis and positioned in the first waist region;
   a second waist panel comprising an inboard lateral edge, an outboard lateral edge, and two longitudinal edges, the second waist panel comprising a second elastic film bonded to a second nonwoven in a stretched state, and wherein the second waist panel is connected with the chassis and positioned in the second waist region; and
   wherein the first waist panel is bonded with the chassis with a first region of first pressure bonds, the first region of first pressure bonds extending longitudinally inboard from the outboard lateral edge of the first waist panel by a first distance D1;
   wherein the second waist panel is bonded with the chassis with a second region of second pressure bonds, the second region of second pressure bonds extending longitudinally inboard from the outboard lateral edge of the second waist panel by a second distance D2, wherein D1 is greater than D2; and
   wherein the first pressure bonds and the second pressure bonds impart different stretch characteristics to the first and second waist panels, respectively.

2. The absorbent article of claim 1, wherein regions of the first waist panel adjacent the outboard lateral edge and the longitudinal edges are bonded to the chassis and at least a portion of the inboard lateral edge of the first waist panel is unattached to the chassis.

3. The absorbent article of claim 2, wherein regions of the second waist panel adjacent the outboard lateral edge and the longitudinal edges are bonded to the chassis and a least a portion of the inboard lateral edge of the second waist panel is unattached to the chassis.

4. The absorbent article of claim 1, wherein a region adjacent the outboard lateral edge of the second waist panel is adhesively bonded to the chassis and regions adjacent the longitudinal edges of the second waist panel are pressure bonded to the leg gasketing elements.

5. The absorbent article of claim 4, wherein the leg gasketing elements comprise inner cuffs and outer cuffs.

6. The absorbent article of claim 5, wherein the regions adjacent the longitudinal edges of the second waist panel are pressure bonded to the inner cuffs of the leg gasketing elements.

7. The absorbent article of claim 1, wherein a region adjacent the outboard lateral edge of the first waist panel is mechanically bonded to the chassis.

8. The absorbent article of claim 1, wherein the outboard lateral edge of the second waist panel is coterminous with the second waist edge, and wherein the outboard lateral edge of the first waist panel is coterminous with the first waist edge.

9. The absorbent article of claim 1, wherein the outboard lateral edge of the second waist panel is positioned longitudinally inboard of the second waist edge.

10. The absorbent article of claim 1, wherein a region of the second waist panel that is unattached to the chassis comprises an area of about 400 mm$^2$ to about 10000 mm$^2$.

11. The absorbent article of claim 1, wherein the first waist region comprises a front waist region and the second waist region comprises a back waist region.

* * * * *